US012747213B2

(12) United States Patent
Cheung et al.

(10) Patent No.: US 12,747,213 B2
(45) Date of Patent: Sep. 29, 2026

(54) MEMBRANE-ACTIVE ANTI-BACTERIAL COMPOUNDS AND USES THEREOF

(71) Applicants: Trustees of Dartmouth College, Hanover, NH (US); Regents of the University of Minnesota, Minneapolis, MN (US)

(72) Inventors: Ambrose Cheung, Hanover, NH (US); Courtney Aldrich, Minneapolis, MN (US); John Schultz, Minneapolis, MN (US)

(73) Assignees: Trustees of Dartmouth College, Hanover, NH (US); Regents of the University of Minnesota, Minneapolis, MN (US)

( * ) Notice: Subject to any disclaimer, the term of this patent is extended or adjusted under 35 U.S.C. 154(b) by 1220 days.

(21) Appl. No.: 17/638,987

(22) PCT Filed: Aug. 31, 2020

(86) PCT No.: PCT/US2020/048776
§ 371 (c)(1),
(2) Date: Feb. 28, 2022

(87) PCT Pub. No.: WO2021/042046
PCT Pub. Date: Mar. 4, 2021

(65) Prior Publication Data

US 2022/0274927 A1 Sep. 1, 2022

Related U.S. Application Data

(60) Provisional application No. 62/894,135, filed on Aug. 30, 2019.

(51) Int. Cl.

| | |
|---|---|
| ***C07D 215/233*** | (2006.01) |
| ***C07D 215/44*** | (2006.01) |
| ***C07D 237/28*** | (2006.01) |
| ***C07D 239/94*** | (2006.01) |
| ***C07D 401/04*** | (2006.01) |
| ***C07D 401/12*** | (2006.01) |
| ***C07D 417/12*** | (2006.01) |
| ***C07D 471/04*** | (2006.01) |

(52) U.S. Cl.
CPC ....... *C07D 215/233* (2013.01); *C07D 215/44* (2013.01); *C07D 237/28* (2013.01); *C07D 239/94* (2013.01); *C07D 401/04* (2013.01); *C07D 401/12* (2013.01); *C07D 417/12* (2013.01); *C07D 471/04* (2013.01)

(58) Field of Classification Search
CPC .............. C07D 215/233; C07D 215/44; C07D 237/28; C07D 239/94; C07D 401/04; C07D 401/12; C07D 417/12; C07D 471/04
USPC .......................................................... 514/248
See application file for complete search history.

(56) References Cited

FOREIGN PATENT DOCUMENTS

WO WO 2011/032050 3/2011
WO WO-2019042470 A1 * 3/2019 ........... C07D 498/06

OTHER PUBLICATIONS

Marull et al., Eu. of Org. Chem., vol. 2003, No. 8, (Mar. 27, 2003), 1576-1588 (Year: 2003).*
Narsaiah et al., Encyc. Reagents for Org. Syn., vol. 7: Sod-Trim (Jan. 1, 2005) (Year: 2005).*
Schlosser et al., Eu. of Org. Chem., vol. 2006, No. 8, (Nov. 30, 2005), 729-734 (Year: 2005).*
WO2019042470 Google Patents English (Year: 2017).*
European Search Report for European patent application No. 20858588.5, Mailed on Aug. 25, 2023.
Yamashkin SA et al., Tautomerism in the series of pyrrolo[2,3-h]-, -[3,2-f]-, -[2,3-f]-, -[3,2-g]-, and -[3,2-h] quinolines Chemistry of Heterocyclic Compounds, Kluwer Academic Publishers-Plenum Publishers, Nl, vol. 4 5, No. 9, Nov. 24, 2009.
Silvija Maracic et al: "Quinoline and ferrocene conjugates: Synthesis, computational study and biological evaluations", Applied Organometallic Chemistry, Longman Group UK, Ltd, Hoboken, USA, vol. 33, No. 1, Nov. 19, 2018 (Nov. 19, 2018).
Marc Marull et al: "Selective and Efficient Structural Elaboration of 2-(Trifluoromethyl)quinolinones", European Journal of Organic Chemistry, Wiley-VCH, DE, vol. 2003, No. 8, Mar. 27, 2003 (Mar. 27, 2003), pp. 1576-1588.
Panda Siva Set al: "New trifluoromethyl quinolone derivatives: Synthesis and investigation of antimicrobial properties", Bioorganic & Medicinal Chemistry Letters, Elsevier, Amsterdam NL, vol. 23, No. 11, Apr. 3, 2013 (Apr. 3, 2013) , pp. 3225-3229.
Search Report for European Patent App. No. 20858588.5, mailed on Dec. 20, 2023.
Narsaiah B et al: "Ethyl 4,4,4-Trifluoroacetoacetate" In: "Encyclopedia of reagents for organic synthesis; vol. 7 : Sod—Trim", Jan. 1, 2005 Jan. 1, 2005), Wiley, Chichester, XP093111055,ISBN: 978-0-470-84289-8DOI 10.1002/047084289X.rn00587.
Manfred Schlosser et al: "Relay Propagation of Crowding: The Trifluoromethyl Group as Both an Emitter and Transmitter of Steric Pressure", European Journal of Organic Chemistry, Wiley-VCH, DE, vol. 2006, No. 3, Nov. 30, 2005 (Nov. 30, 2005), pp. 729-734, XP072112119,ISSN: 1434-193X, DOI: 10.1002/EJOC.200500728.

(Continued)

*Primary Examiner* — Kortney L. Klinkel
*Assistant Examiner* — Grace Ching Hsu
(74) *Attorney, Agent, or Firm* — Farhang Amini; Shackelford, McKinley & Norton, LLP

(57) ABSTRACT

In an embodiment, the present disclosure pertains to methods of inhibiting bacterial growth. Generally, the methods include exposing bacteria to an anti-bacterial compound as disclosed herein. In some embodiments, the exposing occurs in vivo in a subject in order to treat or prevent a bacterial infection. In additional embodiments, the present disclosure pertains to anti-bacterial compounds that are suitable for inhibiting bacterial growth.

10 Claims, 7 Drawing Sheets

(56) References Cited

OTHER PUBLICATIONS

Nguyen et al., "Preparation and antibacterial evaluation of decarboxylated fluoroquinolones", Bioorganic and Medicinal Chemistry Letters, 2011, vol. 21, pp. 5961-5963.
Domagala et al., "Structure-activity and structure-side-effect relationships for the quinolone antibacterials", Journal of Antimicrobial Chemotherapy. 1994. vol. 33, pp. 685-706.
International Search Report and Written Opinion for PCT/US2020/048776. Mailed on Jan. 26, 2021.
Brunner, J. New photolabeling and crosslinking methods. Annu. Rev.Biochem. 62, 483-514. 1993.
Das, R. K., Samanta, A., Xu, M., Su, D., Leong, C., Ghosh, K., Zhai, D., and Chang, Y.-T. Target identification: A challenging step in forward chemical genetics. Bio.Cent. 3, 1-16. 2011.
Lilienkampf, A., J. Mao, B. Wang, S. G. Franzblau, and A. P. Kozikowski. 2009. Structure-activity relationship for a series of quinolone-based compounds active against replication and non-replicating *Mycobacterium tuberculosis*. J. Med.Chem. 52:2109-2118.
Worthington, R. J .; Melander, C .. 2013. Combination Approaches to Combat Multi-Drug Resistant Bacteria. Trends Biotechnol. 31:177-184.
Nair, D. R., J. Chen, J. M. Monteiro, M. Josten, M. G. Pinho, H. G. Sahl, J. Wu, and A. Cheung. 2017. A quinolinol-based small molecule with anti-MRSA activity that targets bacterial membrane and promotes fermentative metabolism. J.Antibiot.(Tokyo) 70:1009-1019. doi:ja201779 [pil];10.1038/ja.2017.79 [doi].

* cited by examiner

DAPTOMYCIN
MOLECULAR WEIGHT: 1629
tPSA: 695.3

POLYMYXIN $B_1$
MOLECULAR WEIGHT: 1209
tPSA: 498.7

$HArgGlnTyrMetArgGlnIleGluGlnAlaLeuArgTyrGlyTyrArgIleSerArgArgNH_2$
GUAVANIN 2
MOLECULAR WEIGHT: 2.65 kD
tPSA: 1240.9

CD437

CD1530

MOLECULAR WEIGHT: 398
tPSA: 60.36

DNAC-2

1

MEMBRANE-ACTIVE ANTI-BACTERIAL COMPOUNDS AND USES THEREOF

CROSS-REFERENCE TO RELATED APPLICATIONS

This application claims priority to U.S. Provisional Patent Application No. 62/894,135, filed on Aug. 30, 2019. The entirety of the aforementioned application is incorporated herein by reference.

STATEMENT REGARDING FEDERALLY SPONSORED RESEARCH

This invention was made with government support under R21 AI130540 and RO1 AI146116 awarded by the National Institutes of Health. The government has certain rights in the invention.

BACKGROUND

The emergence of multidrug-resistant (MDR) gram-positive bacteria is on the rise. Although antibiotic stewardship and infection control measures are helpful, new agents against MDR gram-positive bacteria are needed. Various embodiments of the present disclosure address the aforementioned needs.

SUMMARY

In an embodiment, the present disclosure pertains to a method of inhibiting bacterial growth. Generally, the method includes exposing bacteria to an anti-bacterial compound. In some embodiments, the anti-bacterial compound has a general structure of:

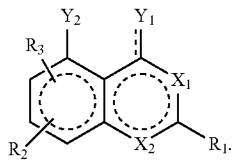

In some embodiments, the exposing occurs in vivo in a subject in order to treat or prevent a bacterial infection in the subject. In an additional embodiment, the present disclosure pertains to one or more anti-bacterial compounds that have the following general structure:

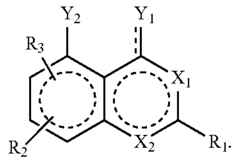

DETAILED DESCRIPTION

It is to be understood that both the foregoing general description and the following detailed description are illustrative and explanatory, and are not restrictive of the subject matter, as claimed. In this application, the use of the singular includes the plural, the word “a” or “an” means “at least one”, and the use of “or” means “and/or”, unless specifically stated otherwise. Furthermore, the use of the term “including”, as well as other forms, such as “includes” and “included”, is not limiting. Also, terms such as “element” or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Bacterial infections present significant public health concerns. For instance, nosocomial infections caused by resistant Gram-positive ($Gram^+$) organisms are on the rise, presumably due to a combination of factors including prolonged hospital exposure, increased use of invasive procedures, and pervasive antibiotic therapy. Compounding the problem is the emergence of multidrug-resistant (MDR) $Gram^+$ bacteria, such as methicillin-resistant *Staphylococcus aureus* (MRSA), *Staphylococcus epidermidis, Streptococcus pneumoniae*, and *Enterococcus* spp., which render treatment extremely difficult.

As a result, last resort antibiotics, such as vancomycin, linezolid, and daptomycin are frequently used as a treatment for infections caused by MDR $Gram^+$ bacteria, which have the unintended consequence of selecting resistance to these agents. Although antibiotic stewardship and infection control measures are helpful, new anti-bacterial agents against MDR $Gram^+$ bacteria are needed.

More generally, a need exists for more effective anti-bacterial compounds and methods for inhibiting the growth of various bacteria and treating various bacterial infections. Embodiments of the present disclosure address the aforementioned need.

Figure 1A:
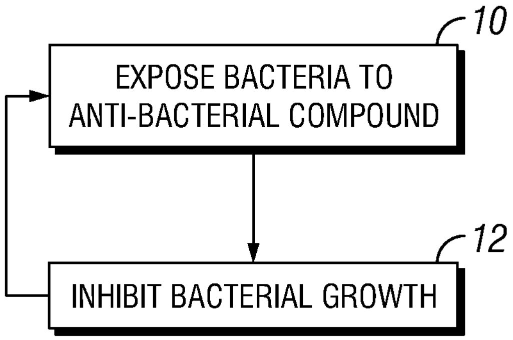
FIG. 1A illustrates a method to inhibit bacterial growth according to an aspect of the present disclosure.
Figure 1B:
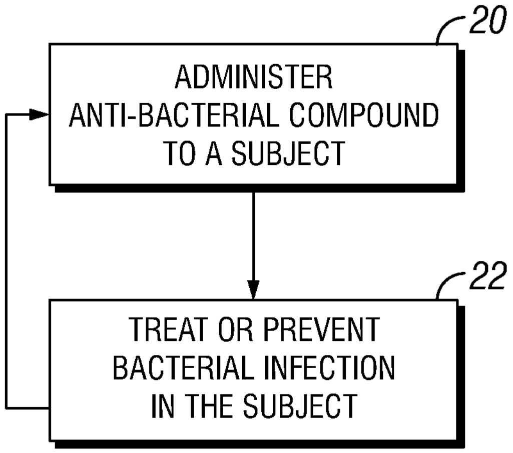
FIG. 1B illustrates a method of treating or preventing a bacterial infection in a subject by administering to the subject an anti-bacterial compound of the present disclosure.

In some embodiments, the present disclosure pertains to methods of inhibiting bacterial growth. In some embodiments illustrated in FIG. 1A, the methods of the present disclosure generally include one or more of the following steps of: exposing bacteria to an anti-bacterial compound (step 10); and inhibiting bacterial growth (step 12). In some embodiments illustrated in FIG. 1B, the exposing can occur via administration of the anti-bacterial compound to a subject (step 20) in order to treat or prevent a bacterial infection in a subject (step 22).

In some embodiments, the methods of the present disclosure can be repeated until the bacteria and/or the bacterial infection are eliminated. In some embodiments, the anti-bacterial compound exposed to the bacteria has the following base structure:

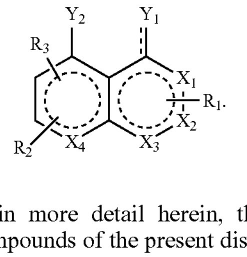

As set forth in more detail herein, the methods and anti-bacterial compounds of the present disclosure can have numerous embodiments. For instance, the methods of the present disclosure can utilize various anti-bacterial compounds that have various chemical structures and functional groups. Furthermore, the anti-bacterial compounds of the present disclosure may be utilized to inhibit bacterial growth in various subjects for the treatment or prevention of various bacterial infections in the subject.

Anti-Bacterial Compounds

The methods of the present disclosure can utilize various types of anti-bacterial compounds for inhibition of bacterial growth. Moreover, the anti-bacterial compounds of the present disclosure can include various chemical configurations and functional groups.

For example, in some embodiments, the anti-bacterial compounds of the present disclosure have the following general structure:

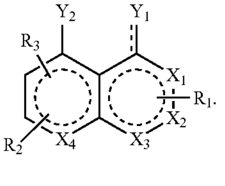

In some embodiments, $Y_1$ includes, without limitation, O, OH, H, F, $R_4$—O, $R_4$—NMe, $R_4$—N(C═O), $R_4$—NH, $CF_3$, $CHF_2$, $CH_2F$, alky($C_1$-$C_4$), methoxy, thiomethyl, cyano, nitro, fluoro, chloro, bromo, iodo, cycloalkyl($C_3$-$C_6$), a heterocyclic, an aromatic, a morpholine, a pyrrolidine, an indolone, an alkyl, a cycloalkyl, an alkenyl, a cycloalkenyl, an alkynyl, a cycloalkynyl, an alkyloxy, a cycloalkyloxy, an alkanoyl, an alkyloxycarbonyl, alkyloxycarbonyloxy, an aryl, an aryl alcohol, an aryl alkyl, an aryl halo, a heteroaryl, a heterocycle, a phenyl, a pyridyl, an amino, a pyridyl amino, a pyridazine, a ketone, an aryl ketone, an oxime, an aryl oxime, an imine, an aryl imine, an aryl nitrile, an amide, an aryl amide, an aryl nitro, an aryl carbamate, a carbamate, an aldehyde, an aryl aldehyde, a hemiacetal, an aryl hemiacetal, a carboxylic acid, an aryl carboxylic acid, a ester, an aryl ester, an ether, an aryl ether, a thiol, an aryl thiol, a disulfide, a sulfoxide, a sulfone, a sulfonamide, pyrrol-2-yl, pyrrol-3-yl, pyrrol-2-ylamino, 1-methylpyrrol-2-yl, 1-methylpyrrol-3-yl, 1-methylpyrrol-2-ylamino, morpholino, piperazinyl, 3,4-dichloroanilino, 3,4-difluoroanilino, 5-(trifluoromethyl)pyridin-2-yl-amino, piperazin-1-yl, 5-(trifluoromethyl)pyridin-2-yl-amino, thiazol-2-ylamino, 5-(trifluoromethyl)pyridin-2-yl-amino, 3,4-dichloroanilino, 3-(trifluoromethoxy)aniline, 5-(fluoro)pyridin-2-yl-amino, 5-dimethylaminopyridin-2-yl-amino, 6-(trifluoromethyl) pyridazine-3-yl-amino, (N,N-dimethyl-6-sulfamoyl)pyridin-2-yl-amino, 1H-indazol-4-yl-amino, 4-(trifluoromethyl) cyclohexyl, 4-(trifluoromethyl)cyclohexyl-amino,

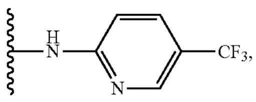, 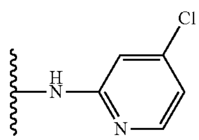,

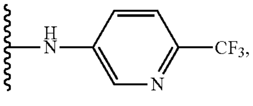, 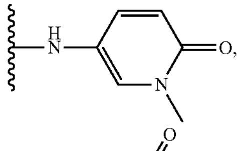,

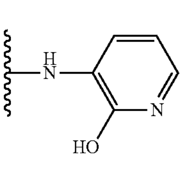, 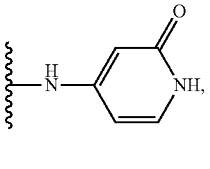,

-continued

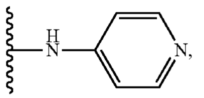
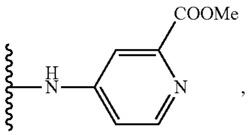
,

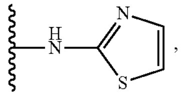
,
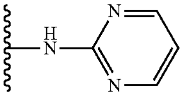
,

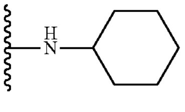
,
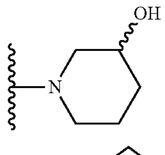
,

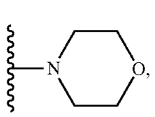
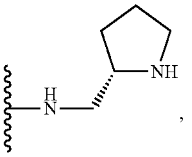
,

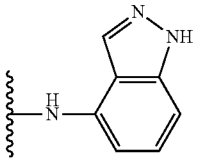
,
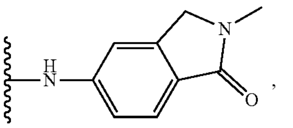
,

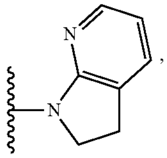
,
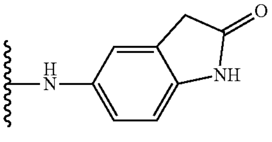
, and

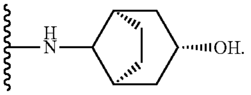

In some embodiments, $Y_2$ includes, without limitation, H, F, $R_4$—O, $R_4$—NMe, $R_4$—N(C═O), $R_4$—NH, $CF_3$, $C_1$, Br, cyano, nitro, $CF_3$, $CHF_2$, $CH_2F$, a heterocyclic, an aromatic, a morpholine, a pyrrolidine, an indolone, an alkyl, a cycloalkyl, an alkenyl, a cycloalkenyl, an alkynyl, a cycloalkynyl, an alkyloxy, a cycloalkyloxy, an alkanoyl, an alkyloxycarbonyl, alkyloxycarbonyloxy, an aryl, an aryl alcohol, an aryl alkyl, an aryl halo, a heteroaryl, a heterocycle, a phenyl, a pyridyl, an amino, a pyridyl amino, a pyridazine, a ketone, an aryl ketone, an oxime, an aryl oxime, an imine, an aryl imine, an aryl nitrile, an amide, an aryl amide, an aryl nitro, an aryl carbamate, a carbamate, an aldehyde, an aryl aldehyde, a hemiacetal, an aryl hemiacetal, a carboxylic acid, an aryl carboxylic acid, a ester, an aryl ester, an ether, an aryl ether, a thiol, an aryl thiol, a disulfide, a sulfoxide, a sulfone, a sulfonamide, piperazinyl, 3,4-dichloroanilino, 3,4-difluoroanilino, 3-(trifluoromethoxy)aniline, 5-(trifluoromethyl)pyridin-2-yl-amino, 5-(fluoro)pyridin-2-yl-amino, 5-dimethylaminopyridin-2-yl-amino, 6-(trifluoromethyl)pyridazine-3-yl-amino, (N,N-dimethyl-6-sulfamoyl)pyridin-2-yl-amino, 1H-indazol-4-yl-amino, 4-(trifluoromethyl)cyclohexyl-amino, pyrrol-2-yl, pyrrol-3-yl, pyrrol-2-ylamino, 1-methylpyrrol-2-yl, 1-methylpyrrol-3-yl, 1-methylpyrrol-2-ylamino, piperazinyl morpholino, $R_6$—NH, alky($C_1$-$C_4$), cycloalkyl($C_3$-$C_6$), methoxy, thiomethyl, 3-(trifluoromethoxy)anilino,

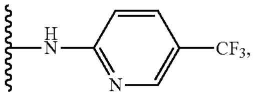
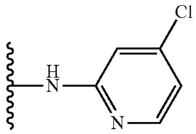
,

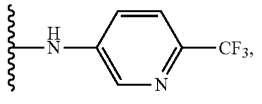
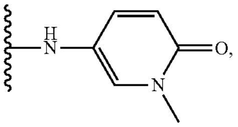

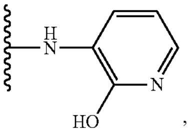
,
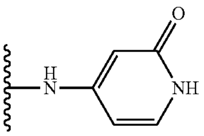
,

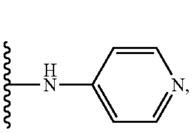
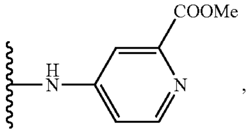
,

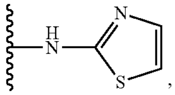
,
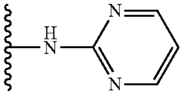
,

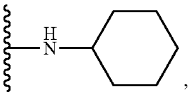
,
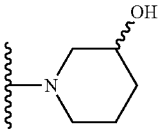
,
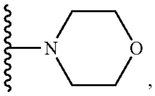
,

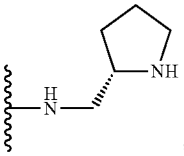
,
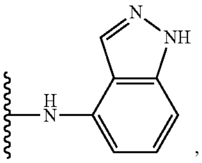
,

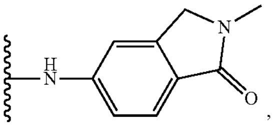
,
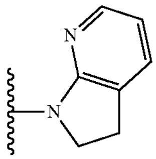
,

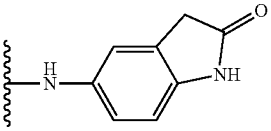
, and

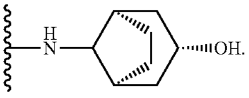

In some embodiments, $R_6$ is

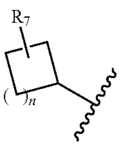

and n is an integer that can be 0 to 5. In some embodiments, $R_7$ can include, without limitation, H, F, $CF_3$, $CHF_2$, $CH_2F$, alky($C_1$-$C_4$), methoxy, thiomethyl, and cyano. In some embodiments, $Y_2$ can include, without limitation, an aryl thiol, a disulfide, a sulfoxide, a sulfone, a sulfonamide, pyrrol-2-yl, pyrrol-3-yl, pyrrol-2-ylamino, 1-methylpyrrol- 2-yl, 1-methylpyrrol-3-yl, 1-methylpyrrol-2-ylamino, morpholino, piperazinyl, piperazin-1-yl, and combinations thereof.

In some embodiments, $X_1$, $X_2$, $X_3$, and $X_4$ each independently include, without limitation, C, CH, CF, C—$R_9$, N, NH, and N—$R_9$.

In some embodiments, $R_1$, $R_2$, $R_3$, $R_4$, and $R_9$, each independently include, without limitation, H, F, —$CHF_2$, —$CH_2F$, —$CF_3$, —$OCF_3$, —OMe, —$S(O)_2N(Me)_2$, azido, cyano, nitro, thiomethyl, methoxy, alkyl($C_1$-$C_4$)ester, alky ($C_1$-$C_4$), chloro, bromo, fluoro, iodo ethyl, benzylether, methoxy, a benzonitrile, a pyridyl, a pyridyl amino, an aniline, an amino, piperazinyl, a morpholine, a pyrrolidine, an indolone, an anilino, 3,4-difluorophenyl, a pyridazine, a heterocyclic, an aromatic, an alkyl, a cycloalkyl, an alkenyl, a cycloalkenyl, an alkynyl, a cycloalkynyl, an alkyloxy, a cycloalkyloxy, an alkanoyl, an alkyloxycarbonyl, alkyloxycarbonyloxy, an aryl, an aryl alcohol, an aryl alkyl, an aryl halo, a heteroaryl, a heterocycle, phenyl, a ketone, an aryl ketone, an oxime, an aryl oxime, an imine, an aryl imine, an aryl nitrile, an amide, an aryl amide, an aryl nitro, an aryl carbamate, a carbamate, an aldehyde, an aryl aldehyde, a hemiacetal, an aryl hemiacetal, a carboxylic acid, an aryl carboxylic acid, a ester, an aryl ester, an ether, an aryl ether, a thiol, an aryl thiol, a disulfide, a sulfoxide, a sulfone, a sulfonamide, thiomethyl, 3-(trifluoromethoxy)phenyl, 2-isopropylphenyl, 3-acetylphenyl, 3-benzonitrile, 2-chlorophenyl, 3-chlorophenyl, 4-chlorophenyl, 3-fluorophenyl, 3-bromophenyl, 3-iodophenyl, 3,4-difluorophenyl, 3,4-dichloropheyl, 3-(hydroxymethyl)phenyl, 3-thiomethylphenyl, 3-methoxyphenyl, 3-(trifluoromethyl) phenyl, 3,4-(methylenedioxy)phenyl, 3-(morpholino)phenyl, 4-(morpholino)phenyl, 5-(trifluoromethyl)pyridin-2-yl, thiazol-2-yl, 4-(trifluoromethyl)cyclohexyl, 3,4-dichlorophenyl, 4-trifluoromethylphenyl, 5-(trifluoromethyl)pyridin-2-yl-amino, 3,4-dichloroanilino, 3,4-difluoroanilino, 3-(trifluoromethoxy)aniline, 5-(fluoro)pyridin-2-yl-amino, 5-dimethylaminopyridin-2-yl-amino, 6-(trifluoromethyl) pyridazine-3-yl-amino, (N,N-dimethyl-6-sulfamoyl)pyridin-2-yl-amino, 1H-indazol-4-yl-amino, 4-(trifluoromethyl) cyclohexyl-amino, nitro, cyano, carboxyl, C(O)OMe, C(O) OEt, azido, $R_6$—NH, and morpholino. In some embodiments, $R_6$ is

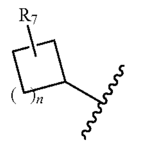

and n is an integer that can be between 0 to 5. In some embodiments, $R_7$ can include, without limitation, H, F, $CF_3$, $CHF_2$, $CH_2F$, alky($C_1$-$C_4$), methoxy, thiomethyl, and cyano. In some embodiments, $R_1$, $R_2$, $R_3$, $R_4$, and $R_9$, can include, without limitation, —C(═O)OH, tetrazolyl, 5-(fluoro)pyridin-2-yl, 5-dimethylaminopyridin-2-yl, 6-(trifluoromethyl) pyridazine-3-yl, 6-(fluoro)pyridazine-3-yl, (N,N-dimethyl-6-sulfamoyl)pyridin-2-yl, 1H-indazol-4-yl, 4-(trifluoromethyl)cyclohexyl, thiazol-2-yl, tetrazolyl, azido, cyano, nitro, thiomethyl, methoxy, alkyl($C_1$-$C_4$)ester, alky($C_1$-$C_4$), thiazol-2-yl-amino, and combinations thereof.

In some embodiments, the anti-bacterial compounds of the present disclosure include, without limitation:

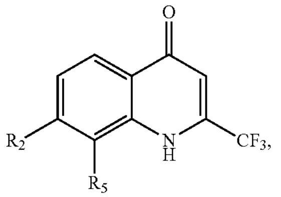
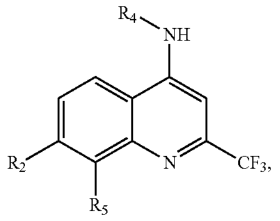
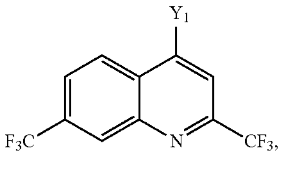
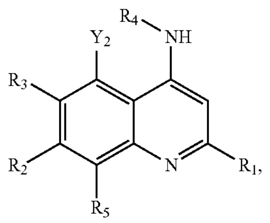
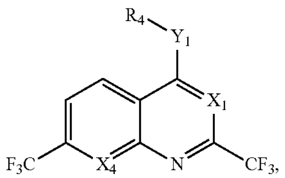
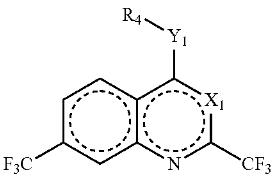
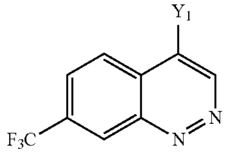
,
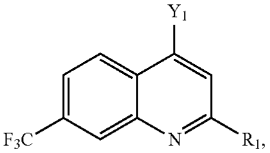
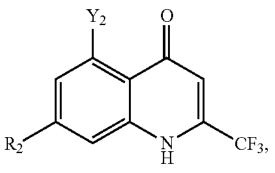

tautomers thereof, and combinations thereof.

In particular embodiments, the anti-bacterial compounds of the present disclosure include the following structure:

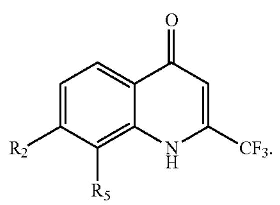

In some embodiments, $R_2$ and $R_5$ each independently include, without limitation, H, F, $CF_3$, $OCF_3$, chloro, bromo, ethyl, benzylether, methoxy, thiomethyl, nitro, cyano, carboxyl, C(O)OMe, C(O)OEt, and azido. In some embodiments, the anti-bacterial compound includes a tautomer of the aforementioned structure.

In particular embodiments, the anti-bacterial compounds of the present disclosure include the following structure:

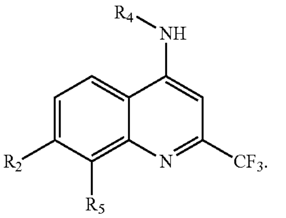

In some embodiments, $R_2$, $R_4$, and $R_5$ each independently include, without limitation, H, $CF_3$, $OCF_3$, OMe, $S(O)_2N(Me)_2$, 3-(trifluoromethoxy)phenyl, phenyl, 2-isopropylphenyl, 3-acetylphenyl, 3-benzonitrile, 2-chlorophenyl, 3-chlorophenyl, 4-chlorophenyl, 3-fluorophenyl, 3-bromophenyl, 3-iodophenyl, 3,4-difluorophenyl, 3,4-dichloropheyl, 3-(hydroxymethyl)phenyl, 3-thiomethylphenyl, 3-methoxyphenyl, 3-(trifluoromethyl)phenyl, 3,4-(methylenedioxy)phenyl, 3-(morpholino)phenyl, 4-(morpholino)phenyl, 5-(trifluoromethyl)pyridin-2-yl, and 3,4-dichlorophenyl. In some embodiments, $R_2$ and $R_5$ can include, without limitation, H, $CF_3$, $OCF_3$, OMe, $S(O)_2N(Me)_2$. In some embodiments, $R_4$ can include, without limitation, H, Me, phenyl, cyclohexyl, pyridin-2-yl, 3-(trifluoromethoxy)phenyl, 2-isopropylphenyl, 3-acetylphenyl, 3-benzonitrile, 2-chlorophenyl, 3-chlorophenyl, 4-chlorophenyl, 3-fluorophenyl, 4-fluorophenyl, 3-bromophenyl, 3-iodophenyl, 3,4-difluorophenyl, 3,4-dichloropheyl, 3-(hydroxymethyl)phenyl, 3-thiomethylphenyl, 3-methoxyphenyl, 3-(trifluoromethyl)phenyl, 3,4-(methylenedioxy)phenyl, 3-(morpholino)phenyl, 4-(morpholino)phenyl, 5-(trifluoromethyl)pyridin-2-yl, 1H-indazol-4-yl, 4-(trifluoromethyl)cyclohexyl, and thiazol-2-yl. In some embodiments, the anti-bacterial compound includes a tautomer of the aforementioned structure.

In particular embodiments, the anti-bacterial compounds of the present disclosure include the following structure:

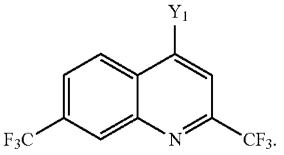

In some embodiments, $Y_1$ includes, without limitation:

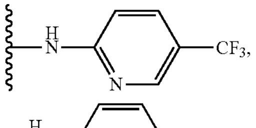
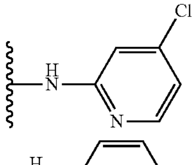,
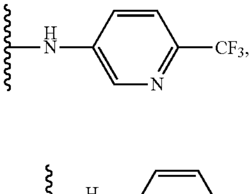
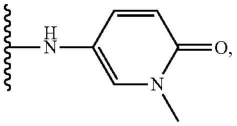
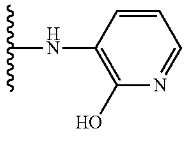,
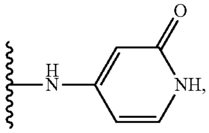

-continued

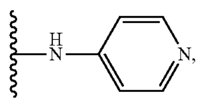
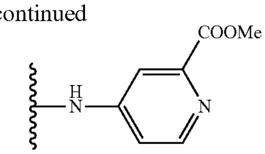,
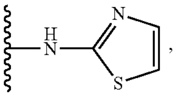,
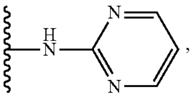,
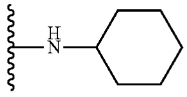,
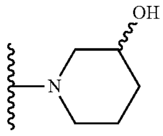,
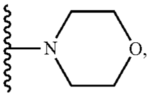
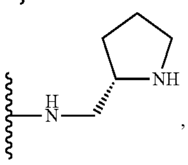,
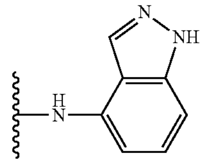,
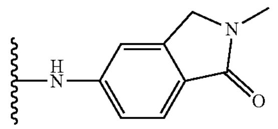,
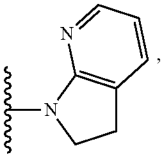,
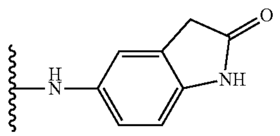, and
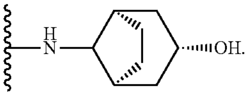

In some embodiments, $Y_1$ can include, without limitation, thiazol-2-ylamino, 5-(trifluoromethyl)pyridin-2-yl-amino, 3,4-dichloroanilino, 3,4-difluoroanilino, 3-(trifluoromethoxy)aniline, 5-(fluoro)pyridin-2-yl-amino, 5-dimethylaminopyridin-2-yl-amino, 6-(trifluoromethyl)pyridazine-3-yl-amino, (N,N-dimethyl-6-sulfamoyl)pyridin-2-yl-amino, 1H-indazol-4-yl-amino, 4-(trifluoromethyl)cyclohexyl, and 4-(trifluoromethyl)cyclohexyl-amino. In some embodiments, the anti-bacterial compound includes a tautomer of the aforementioned structure.

In particular embodiments, the anti-bacterial compounds of the present disclosure include the following structure:

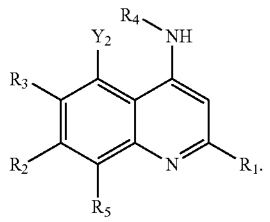

In some embodiments, $Y_2$ includes, without limitation, H and F.

In some embodiments, $R_1$, $R_2$, $R_3$, $R_4$, and $R_5$ each independently include, without limitation, H, F, Cl, Br, cyano, nitro, $CF_3$, $CHF_2$, 3,4-dichlorophenyl, 3-(trifluoromethoxy)phenyl, and 5-(trifluoromethyl)pyridin-2-yl. In some embodiments, $R_4$ can include, without limitation, 3,4-difluorophenyl, 3,4-dichlorophenyl, 3-(trifluoromethoxy)phenyl, and 5-(trifluoromethyl)pyridin-2-yl. In some embodiments, the anti-bacterial compound includes a tautomer of the aforementioned structure.

In particular embodiments, the anti-bacterial compounds of the present disclosure include the following structure:

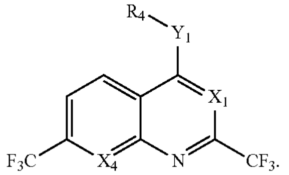

In some embodiments, $Y_1$ includes, without limitation, O, NMe, N(C═O), and NH.

In some embodiments, $X_1$ and $X_4$ each independently include, without limitation, CH and N.

In some embodiments, $R_4$ includes, without limitation, 3-chlorophenyl, 3-fluorophenyl, 3,4-dichlorophenyl, 3-(trifluoromethoxy)phenyl, 4-trifluoromethylphenyl, 5-(trifluoromethyl)pyridin-2-yl, and 3,4-difluorophenyl. In some embodiments, the anti-bacterial compound includes a tautomer of the aforementioned structure.

In particular embodiments, the anti-bacterial compounds of the present disclosure include the following structure:

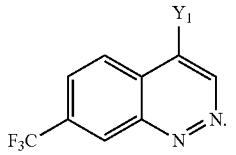

In some embodiments, $Y_1$ includes, without limitation, 3,4-difluoroanilino and 5-(trifluoromethyl)pyridin-2-yl-amino.

In particular embodiments, the anti-bacterial compounds of the present disclosure include the following structure:

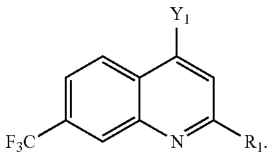

In some embodiments, $Y_1$ includes, without limitation, H, F, Cl, Br, $CF_3$, $CHF_2$, $CH_2F$, piperazinyl, 5-(trifluoromethyl) pyridin-2-yl-amino, and morpholino.

In some embodiments, $R_1$ includes, without limitation, H, F, Cl, Br, $CF_3$, $CHF_2$, $CH_2F$, piperazinyl, 5-(trifluoromethyl) pyridin-2-yl-amino, and morpholino. In some embodiments, the anti-bacterial compound includes a tautomer of the aforementioned structure.

In particular embodiments, the anti-bacterial compounds of the present disclosure include the following structure:

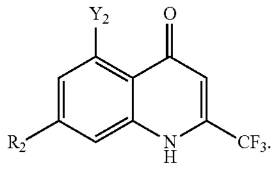

In some embodiments, $Y_2$ includes, without limitation, H, F, —$CHF_2$, —$CH_2F$, —$CF_3$, —$OCF_3$, —OMe, —$S(O)_2N(Me)_2$, —C(═O)OH, tetrazolyl, azido, cyano, nitro, thiomethyl, methoxy, alkyl($C_1$-$C_4$)ester, alky($C_1$-$C_4$), phenyl, cyclohexyl, pyridin-2-yl, 3,4-dichloroanilino, 3,4-difluoroanilino, 3-(trifluoromethoxy)aniline, 5-(trifluoromethyl)pyridin-2-yl-amino, 5-(fluoro)pyridin-2-yl-amino, 5-dimethylaminopyridin-2-yl-amino, 6-(trifluoromethyl)pyridazine-3-yl-amino, pyridazine-3-yl-amino, pyridazine-3-yl, (N,N-dimethyl-6-sulfamoyl)pyridin-2-yl-amino, 1H-indazol-4-yl-amino, 4-(trifluoromethyl)cyclohexyl-amino, pyrrol-2-yl, pyrrol-3-yl, pyrrol-2-ylamino, 1-methylpyrrol-2-yl, 1-methylpyrrol-3-yl, 1-methylpyrrol-2-ylamino, piperazinyl, and morpholino.

In some embodiments, $R_2$ includes, without limitation, F, $CF_3$, 3,4-dichloroanilino, 3,4-difluoroanilino, 3-(trifluoromethoxy)aniline, 5-(trifluoromethyl)pyridin-2-yl-amino, 5-(fluoro)pyridin-2-yl-amino, 5-dimethylaminopyridin-2-yl-amino, 6-(trifluoromethyl)pyridazine-3-yl-amino, (N,N-dimethyl-6-sulfamoyl)pyridin-2-yl-amino, 1H-indazol-4-yl-amino, 4-(trifluoromethyl)cyclohexyl-amino, and morpholino. In some embodiments, the anti-bacterial compound includes a tautomer of the aforementioned structure.

In some embodiments, the anti-bacterial compounds of the present disclosure include the following structure:

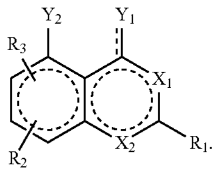

In some embodiments, $Y_1$ and $Y_2$ can be any of the above mentioned $Y_1$ and $Y_2$ functional groups. In some embodiments, $X_1$ and $X_2$ can be any of the $X_1$, $X_2$, $X_3$, or $X_4$ groups as discussed above. In some embodiments, $R_1$, $R_2$, and $R_3$, can be any of the aforementioned $R_1$, $R_2$, $R_3$, $R_4$, and $R_5$ groups.

In some embodiments, $Y_1$ can include, without limitation, ═O, —OH, —H, —F, —O—$R_4$, —N(Me)-$R_4$, —N(C═O)$R_4$, —C(═O)$R_4$, —NH—$R_4$, —$CF_3$, —$CHF_2$, —$CH_2F$, alky($C_1$-$C_4$), methoxy, thiomethyl, cyano, nitro, fluoro, chloro, bromo, iodo, cycloalkyl($C_3$-$C_6$), an alkenyl($C_3$-$C_6$) group, a cycloalkenyl($C_3$-$C_6$) group, an alkynyl($C_3$-$C_6$) group, a cycloalkynyl, an alkyloxy, a cycloalkyloxy, an alkanoyl, an alkyloxycarbonyl, alkyloxycarbonyloxy, an aryl, an aryl alcohol, an aryl alkyl, an aryl halo, a heteroaryl, a heterocycle, a phenyl, a pyridyl, an amino, a pyridyl amino, an indolone, a pyridazine, an aryl ketone, an oxime, an aryl oxime, an imine, an aryl imine, an aryl nitrile, an amide, an aryl amide, an aryl nitro, an aryl carbamate, a carbamate, an aldehyde, an aryl aldehyde, a hemiacetal, an aryl hemiacetal, a carboxylic acid, an aryl carboxylic acid, a ester, an aryl ester, an ether, an aryl ether, a thiol, an aryl thiol, a disulfide, a sulfoxide, a sulfone, a sulfonamide, pyrrol-2-yl, pyrrol-3-yl, pyrrol-2-ylamino, 1-methylpyrrol-2-yl, 1-methylpyrrol-3-yl, 1-methylpyrrol-2-ylamino, morpholino, and piperazinyl, 3,4-dichloroanilino, 3,4-difluoroanilino, 5-(trifluoromethyl)pyridin-2-yl-amino, piperazin-1-yl, 5-(trifluoromethyl)pyridin-2-yl-amino, morpholino,

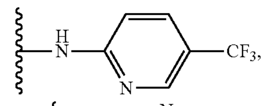
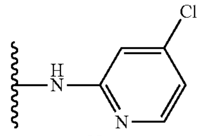
,
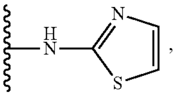
,
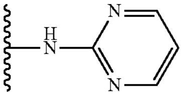
,
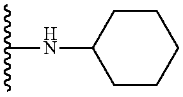
,
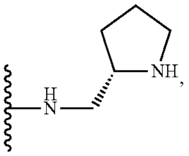
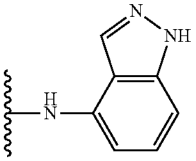
,
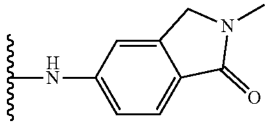
,
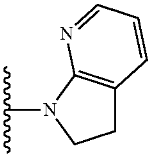
, and
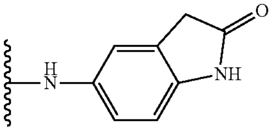
.

In some embodiments, $Y_2$ can include, without limitation, —S—$R_4$, —O—$R_4$, —O—N═CH—$R_4$, —N(Me)-$R_4$, —N(C═O)$R_4$, —NH—$R_4$, —C(═O)$R_4$, —C(═O)O—$R_4$, —NH—$R_4$—C(═O)OH, —NH—$R_4$—C(═O)$NH_2$, —NH—$R_4$—$NO_2$, —NH—$R_4$—CN, —NH—$R_4$—$CF_3$, —NH—$R_4$—F, —NH—$R_4$—$CHF_2$, —NH—$R_4$—$CH_2F$, —$R_4$-alky($C_1$-$C_4$), —H, —F, —$CF_3$, —$CHF_2$, —$CH_2F$, alky($C_1$-$C_4$), a heterocyclic, an aromatic, methoxy, thiomethyl, cyano, nitro, chloro, bromo, iodo, cycloalkyl($C_3$-$C_6$), an alkenyl($C_3$-$C_6$) group, a cycloalkenyl($C_3$-$C_6$) group, an alkynyl($C_3$-$C_6$) group, a cycloalkyl($C_3$-$C_7$)oxy, an alkyl($C_1$-$C_4$)oxycarbonyl, alkyl($C_1$-$C_4$), an alkyl($C_1$-$C_4$)oxycarbonyloxymethyl group, a branched alkyl($C_4$-$C_8$)oxycarbonyloxymethyl group, phenyl, an aryl alcohol, a phenylalkyl ($C_1$-$C_4$), an aryl halo, a pyridyl, a pyridyl amino, an indolone, a pyridazine, an aryl ketone, an aryl oxime, an imine, an aryl imine, an aryl nitrile, an amide, an aryl amide, an aryl nitro, an aryl carbamate, a carbamate, an aldehyde, an aryl aldehyde, a hemiacetal, an aryl hemiacetal, an aryl thiol, a disulfide, a sulfoxide, a sulfone, a sulfonamide, pyrrol-2-yl, pyrrol-3-yl, pyrrol-2-ylamino, 1-methylpyrrol-2-yl, 1-methylpyrrol-3-yl, 1-methylpyrrol-2-ylamino, morpholino, and piperazinyl, piperazin-1-yl, morpholino, a thiol, an aryl thiol, a disulfide, a sulfoxide, a sulfone, a sulfonamide, piperazinyl, 3,4-dichloroanilino, 3,4-difluoroanilino, 3-(trifluoromethoxy)aniline, 5-(trifluoromethyl)pyridin-2-yl-amino, 5-(fluoro)pyridin-2-yl-amino, 5-dimethylaminopyridin-2-yl-amino, 6-(trifluoromethyl)pyridazine-3-yl-amino, (N,N-dimethyl-6-sulfamoyl)pyridin-2-yl-amino, 1H-indazol-4-yl-amino, 4-(trifluoromethyl)cyclohexyl-amino,

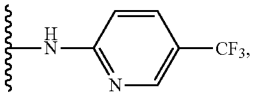
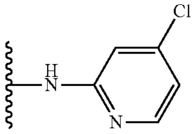
,
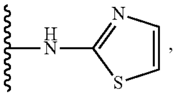
,
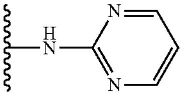
,
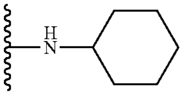
,
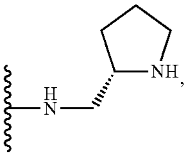
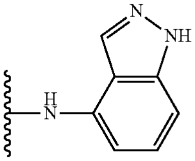
,
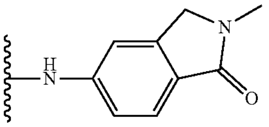
,
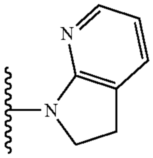
, and
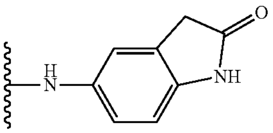
.

In some embodiments, $X_1$ and $X_2$, can include, without limitation, C, CH, CF, C—$R_9$, N, NH, and N—$R_9$.

In some embodiments, $R_1$ can include, without limitation, H, F, —$CHF_2$, —$CH_2F$, —$CF_3$, —$OCF_3$, —OMe, —$S(O)_2N(Me)_2$, —C(═O)OH, tetrazolyl, azido, cyano, nitro, thiomethyl, methoxy, alkyl($C_1$-$C_4$)ester, and alky($C_1$-$C_4$).

In some embodiments, $R_4$ and $R_9$ can include, without limitation, phenyl, pyridin-2-yl, pyridizin-3-yl, 3-(trifluoromethoxy)phenyl, 2-isopropylphenyl, 3-acetylphenyl, 3-benzonitrile, 2-chlorophenyl, 3-chlorophenyl, 4-chlorophenyl, 3-fluorophenyl, 4-fluorophenyl, a bromophenyl group, an iodophenyl group, 3,4-difluorophenyl, 3,4-dichloropheyl, 3-(hydroxymethyl)phenyl, 3-thiomethylphenyl, 3-methoxyphenyl, 3-(trifluoromethyl)phenyl, 3,4-(methylenedioxy)phenyl, 3-(morpholino)phenyl, 4-(morpholino)phenyl, 5-(trifluoromethyl)pyridin-2-yl, 3,4-dichlorophenyl, 4-trifluoromethylphenyl, 5-(trifluoromethyl)pyridin-2-yl, 5-(fluoro)pyridin-2-yl, 5-dimethylaminopyridin-2-yl, 6-(trifluoromethyl)pyridazine-3-yl, 6-(fluoro)pyridazine-3-yl, (N,N-dimethyl-6-sulfamoyl)pyridin-2-yl, 1H-indazol-4-yl, 4-(trifluoromethyl)cyclohexyl, and thiazol-2-yl.

In some embodiments, $R_2$ and $R_3$ can include, without limitation, H, F, —$CHF_2$, —$CH_2F$, —$CF_3$, —$OCF_3$, —OMe, —$S(O)_2N(Me)_2$, —C(═O)OH, tetrazolyl, azido, cyano, nitro, thiomethyl, methoxy, alkyl($C_1$-$C_4$)ester, alky ($C_1$-$C_4$), chloro, ethyl, benzylether, methoxy, thiomethyl, a benzonitrile, a pyridyl, a pyridyl amino, an aniline, an amino, piperazinyl, a pyrrolidine, an indolone, an anilino, a pyridazine, a heterocyclic, an aromatic, an alkyl, a cycloalkyl, an alkenyl, a cycloalkenyl, an alkynyl, a cycloalkynyl, an alkyloxy, a cycloalkyloxy, an alkanoyl, an alkyloxycarbonyl, alkyloxycarbonyloxy, an aryl, an aryl alcohol, an aryl alkyl, an aryl halo, a heteroaryl, a heterocycle, phenyl, a ketone, an aryl ketone, an oxime, an aryl oxime, an imine, an aryl imine, an aryl nitrile, an amide, an aryl amide, an aryl nitro, an aryl carbamate, a carbamate, an aldehyde, an aryl aldehyde, a hemiacetal, an aryl hemiacetal, a carboxylic acid, an aryl carboxylic acid, a ester, an aryl ester, an ether, an aryl ether, a thiol, an aryl thiol, a disulfide, a sulfoxide, a sulfone, a sulfonamide, thiomethyl, 3-(trifluoromethoxy) phenyl, 2-isopropylphenyl, 3-acetylphenyl, 3-benzonitrile, 2-chlorophenyl, 3-chlorophenyl, 4-chlorophenyl, 3-fluorophenyl, 3-bromophenyl, 3-iodophenyl, 3,4-difluorophenyl, 3,4-dichloropheyl, 3-(hydroxymethyl)phenyl, 3-thiomethylphenyl, 3-methoxyphenyl, 3-(trifluoromethyl)phenyl, 3,4-(methylenedioxy)phenyl, 3-(morpholino)phenyl, 4-(morpholino)phenyl, 5-(trifluoromethyl)pyridin-2-yl, 3,4-dichlorophenyl, 4-trifluoromethylphenyl, 5-(trifluoromethyl)pyridin-2-yl-amino, 3,4-dichloroanilino, 3,4-difluoroanilino, 3-(trifluoromethoxy)aniline, 5-(fluoro) pyridin-2-yl-amino, 5-dimethylaminopyridin-2-yl-amino, 6-(trifluoromethyl)pyridazine-3-yl-amino, (N,N-dimethyl-6-sulfamoyl)pyridin-2-yl-amino, 1H-indazol-4-yl-amino, 4-(trifluoromethyl)cyclohexyl, 4-(trifluoromethyl)cyclohexyl-amino, thiazol-2-yl-amino, and morpholino.

In particular embodiments, the anti-bacterial compounds of the present disclosure include the following structure:

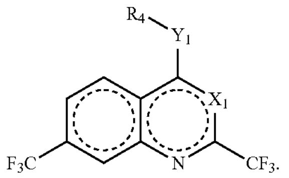

In some embodiments, $Y_1$ can include, without limitation, H, O, NMe, N(C═O), and NH. In some embodiments, $X_1$ can include, without limitation, CH and N. In some embodiments, $R_4$ can include, without limitation, H, Me, phenyl, cyclohexyl, pyridin-2-yl, 3-(trifluoromethoxy)phenyl, 2-isopropylphenyl, 3-acetylphenyl, 3-benzonitrile, 2-chlorophenyl, 3-chlorophenyl, 4-chlorophenyl, 3-fluorophenyl, 4-fluorophenyl, 3-bromophenyl, 3-iodophenyl, 3,4-difluorophenyl, 3,4-dichloropheyl, 3-(hydroxymethyl)phenyl, 3-thiomethylphenyl, 3-methoxyphenyl, 3-(trifluoromethyl) phenyl, 3,4-(methylenedioxy)phenyl, 3,4-dichlorophenyl, 3-(trifluoromethoxy)phenyl, 4-trifluoromethylphenyl, 5-(trifluoromethyl)pyridin-2-yl, 3,4-difluorophenyl, 1H-indazol-4-yl, 4-(trifluoromethyl)cyclohexyl, and thiazol-2-yl.

In particular embodiments, the anti-bacterial compounds of the present disclosure include the following structure:

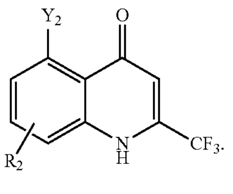

In some embodiments, $Y_2$ and $R_2$ can each independently include, without limitation, $R_6$—NH, F, $CF_3$, $CHF_2$, $CH_2F$, alky($C_1$-$C_4$), cycloalkyl($C_3$-$C_6$), methoxy, thiomethyl, cyano, 3,4-dichloroanilino, 3,4-difluoroanilino, 3-(trifluoromethoxy)anilino, 5-(trifluoromethyl)pyridin-2-yl-amino, 5-(fluoro)pyridin-2-yl-amino, 5-dimethylaminopyridin-2-yl-amino, 6-(trifluoromethyl)pyridazine-3-yl-amino, (N,N-dimethyl-6-sulfamoyl)pyridin-2-yl-amino, 1H-indazol-4-yl-amino, 4-(trifluoromethyl)cyclohexyl-amino, pyrrol-2-yl, pyrrol-3-yl, pyrrol-2-ylamino, 1-methylpyrrol-2-yl, 1-methylpyrrol-3-yl, 1-methylpyrrol-2-ylamino, morpholino, and piperazinyl. In some embodiments, $R_6$ is

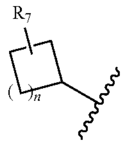

and n is an integer that can be between 0 to 5.

In some embodiments, $R_7$ can include, without limitation, H, F, $CF_3$, $CHF_2$, $CH_2F$, alky($C_1$-$C_4$), methoxy, thiomethyl, and cyano. In some embodiments, the anti-bacterial compound includes a tautomer of the aforementioned structure.

In particular embodiments, the anti-bacterial compounds of the present disclosure include the following structure:

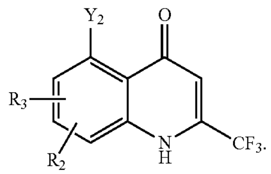

In some embodiments, $Y_2$ and $R_2$ can each include, without limitation, $R_6$—NH, H, F, —$CHF_2$, —$CH_2F$, —$CF_3$, —$OCF_3$, —OMe, —$S(O)_2N(Me)_2$, —C(═O)OH, tetrazolyl, azido, cyano, nitro, thiomethyl, methoxy, alkyl($C_1$-$C_4$)ester, alky($C_1$-$C_4$), 3,4-dichloroanilino, 3,4-difluoroanilino, 3-(trifluoromethoxy)anilino, 5-(trifluoromethyl) pyridin-2-yl-amino, 5-(fluoro)pyridin-2-yl-amino, 5-dimethylaminopyridin-2-yl-amino, 6-(trifluoromethyl) pyridazine-3-yl-amino, (N,N-dimethyl-6-sulfamoyl)pyridin-2-yl-amino, 1H-indazol-4-yl-amino, 4-(trifluoromethyl) cyclohexyl-amino, pyrrol-2-yl, pyrrol-3-yl, pyrrol-2-ylamino, 1-methylpyrrol-2-yl, 1-methylpyrrol-3-yl, 1-methylpyrrol-2-ylamino, morpholino, and piperazinyl.

In some embodiments, $R_3$ can include, without limitation, H, F, —$CHF_2$, —$CH_2F$, —$CF_3$, —$OCF_3$, —OMe, —$S(O)_2N(Me)_2$, —C(═O)OH, tetrazolyl, azido, cyano, nitro, thiomethyl, methoxy, alkyl($C_1$-$C_4$)ester, and alky($C_1$-$C_4$). In some embodiments, $R_6$ is

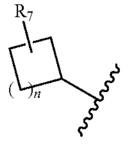

and n is an integer between 0 and 5. In some embodiments, $R_7$ can include, without limitation H, F, Cl, —$CHF_2$, —$CH_2F$, —$CF_3$, —$OCF_3$, —OMe, —$S(O)_2N(Me)_2$, —C(═O)OH, tetrazolyl, azido, cyano, nitro, thiomethyl, methoxy, alkyl($C_1$-$C_4$)ester, and alky($C_1$-$C_4$). In some embodiments, the anti-bacterial compound includes a tautomer of the aforementioned structure.

In particular embodiments, the anti-bacterial compounds of the present disclosure include the following structure:

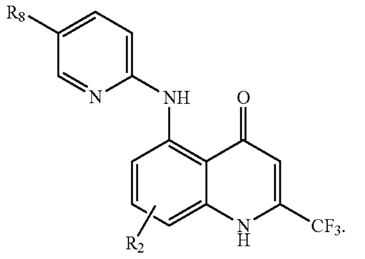

In some embodiments, $R_8$ can include, without limitation, H, F, $CF_3$, $CHF_2$, $CH_2F$, alky($C_1$-$C_4$), methoxy, thiomethyl, cyano, nitro, fluoro, chloro, bromo, and iodo. In some embodiments, $R_2$ can include, without limitation, H, F, OH, $CF_3$, $CHF_2$, $CH_2F$, alky($C_1$-$C_4$), methoxy, thiomethyl, cyano, nitro, fluoro, chloro, bromo, iodo, cycloalkyl($C_3$-$C_6$), morpholino, and piperazinyl. In some embodiments, the anti-bacterial compound includes a tautomer of the aforementioned structure.

In particular embodiments, the anti-bacterial compounds of the present disclosure include the following structure:

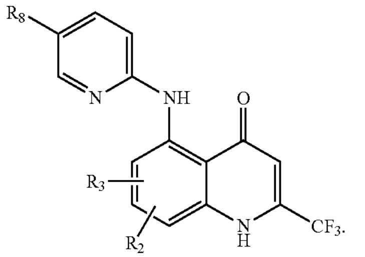

In some embodiments, $R_2$, $R_3$, and $R_8$ can include, without limitation, H, F, —$CHF_2$, —$CH_2F$, —$CF_3$, —$OCF_3$, —OMe, —$S(O)_2N(Me)_2$, —C(=O)OH, tetrazolyl, azido, cyano, nitro, thiomethyl, methoxy, alkyl($C_1$-$C_4$)ester, alky ($C_1$-$C_4$), chloro, bromo, and iodo. In some embodiments, the anti-bacterial compound includes a tautomer of the aforementioned structure.

In particular embodiments, the anti-bacterial compounds of the present disclosure include the following structure:

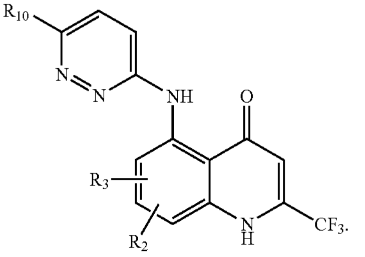

In some embodiments, $R_{10}$ and $R_2$ can include, without limitation, H, F, —$CHF_2$, —$CH_2F$, —$CF_3$, —$OCF_3$, —OMe, —$S(O)_2N(Me)_2$, —C(=O)OH, tetrazolyl, azido, cyano, nitro, thiomethyl, methoxy, alkyl($C_1$-$C_4$)ester, alky ($C_1$-$C_4$), chloro, bromo, iodo, morpholino, and piperazinyl. In some embodiments, $R_3$ can include, without limitation, H, F, —$CHF_2$, —$CH_2F$, —$CF_3$, —$OCF_3$, —OMe, —$S(O)_2N(Me)_2$, —C(=O)OH, tetrazolyl, azido, cyano, nitro, thiomethyl, methoxy, alkyl($C_1$-$C_4$)ester, and alky($C_1$-$C_4$). In some embodiments, the anti-bacterial compound includes a tautomer of the aforementioned structure.

In particular embodiments, the anti-bacterial compounds of the present disclosure include the following structure:

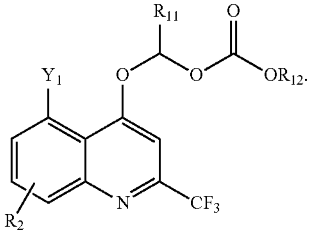

In some embodiments, $Y_1$ and $R_2$ can include, without limitation, $R_6$—NH, F, $CF_3$, $CHF_2$, $CH_2F$, alky($C_1$-$C_4$), cycloalkyl($C_3$-$C_6$), methoxy, thiomethyl, cyano, 3,4-dichloroanilino, 3,4-difluoroanilino, 3-(trifluoromethoxy)anilino, 5-(trifluoromethyl)pyridin-2-yl-amino, 5-(fluoro)pyridin-2-yl-amino, 5-dimethylaminopyridin-2-yl-amino, 6-(trifluoromethyl)pyridazine-3-yl-amino, (N,N-dimethyl-6-sulfamoyl)pyridin-2-yl-amino, 1H-indazol-4-yl-amino, 4-(trifluoromethyl)cyclohexyl-amino, pyrrol-2-yl, pyrrol-3-yl, pyrrol-2-ylamino, 1-methylpyrrol-2-yl, 1-methylpyrrol-3-yl, 1-methylpyrrol-2-ylamino, morpholino, and piperazinyl. In some embodiments, $R_{11}$ includes, without limitation, H, Me, and alky($C_1$-$C_4$). In some embodiments, $R_{12}$ includes, without limitation, Me, alky($C_1$-$C_4$), cycloalkyl ($C_3$-$C_6$), and branched alkyl($C_3$-$C_6$). In some embodiments, $R_6$ is

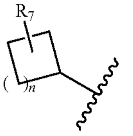

and n is an integer between 0 to 5. In some embodiments, $R_7$ can include, without limitation, H, F, $CF_3$, $CHF_2$, $CH_2F$, alky($C_1$-$C_4$), methoxy, thiomethyl, and cyano. In some embodiments, the anti-bacterial compound includes a tautomer of the aforementioned structure.

In some embodiments, the anti-bacterial compounds of the present disclosure are in a composition. In some embodiments, the compositions of the present disclosure represent therapeutic formulations that enhance or maintain the therapeutic efficacy of the anti-bacterial compounds of the present disclosure.

In some embodiments, the compositions of the present disclosure include one or stabilizers. In some embodiments, the stabilizers include, without limitation, anti-oxidants, sequestrants, ultraviolet stabilizers, or combinations thereof.

In some embodiments, the compositions of the present disclosure include one or more surfactants. In some embodiments, the surfactants include, without limitation, anionic surfactants, cationic surfactants, zwitterionic surfactants, non-ionic surfactants, or combinations thereof.

In some embodiments, the composition of the present disclosure include one or more excipients. In some embodiments, the excipients include, without limitation, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, trehalose, sodium alginate, polyvinylpyrrolidone, polyvinyl alcohol, or combinations thereof.

In some embodiments, the compositions of the present disclosure include a delivery vehicle, such as a particle. In some embodiments, the particle includes, without limitation, lipid-based particles, carbon-based particles, metal-based particles, or combinations thereof.

Inhibition of Bacterial Growth

As set forth in further detail herein, the methods and anti-bacterial compounds of the present disclosure may be utilized to inhibit bacterial growth in various manners via various mechanisms. For instance, in some embodiments, the inhibition of bacterial growth occurs by killing the bacteria. In some embodiments, the inhibition of bacterial growth occurs by disruption of bacterial cell membranes. In some embodiments, the inhibition of bacterial growth occurs by rupturing bacterial cell membranes. In some embodiments, the inhibition of bacterial growth occurs by slowing down bacterial proliferation.

Additionally, as set forth in further detail herein, the methods and anti-bacterial compounds of the present disclosure may be utilized to inhibit the growth of numerous types of bacteria. For instance, in some embodiments, the bacteria includes, without limitation, Gram-positive ($Gram^+$) bacteria, antibiotic resistant $Gram^+$ bacteria, and combinations thereof. In some embodiments, the bacteria includes, without limitation, *Enterococcus faecium, Staphylococcus epidermidis*, methicillin-resistant *Staphylococcus aureus* (MRSA), methicillin-susceptible *Staphylococcus aureus*, and combinations thereof.

Exposure of Bacteria to Anti-Bacterial Compounds

The methods of the present disclosure may be utilized to expose the anti-bacterial compounds of the present disclosure to various bacteria in a variety of manners. For instance, in some embodiments, the exposing occurs in vitro. In some embodiments, the exposing occurs in vivo in a subject. In some embodiments, the subject is suffering from a bacterial infection.

Treatment or Prevention of Bacterial Infections

In some embodiments, the exposure of bacteria to anti-bacterial compounds can occur by the administration of the anti-bacterial compound to a subject. As such, in some embodiments, the present disclosure pertains to methods of treating or preventing a bacterial infection in a subject by administering an anti-bacterial compound of the present disclosure to the subject.

Various methods may be utilized to administer the anti-bacterial compounds of the present disclosure to a subject. For instance, in some embodiments, the administering includes, without limitation, intravenous administration, subcutaneous administration, transdermal administration, topical administration, intraarterial administration, intrathecal administration, intracranial administration, intraperitoneal administration, intraspinal administration, intranasal administration, intraocular administration, oral administration, intratumor administration, and combinations thereof.

In some embodiments, the anti-bacterial compounds of the present disclosure are co-administered to a subject with one or more active agents. For instance, in some embodiments, the one or more active agents include oxacillin.

The methods of the present disclosure can be utilized to treat or prevent bacterial infections in various subjects. For instance, in some embodiments, the subject is suffering from a bacterial infection, and the methods of the present disclosure are utilized to treat the bacterial infection in the subject. In some embodiments, the subject is vulnerable to a bacterial infection, and the methods of the present disclosure are utilized to prevent the bacterial infection in the subject.

In some embodiments, the subject is a human being. In some embodiments, the subject is an animal, such as cattle, dogs, cats, sheep, cattle, horses, and various livestock.

Applications and Advantages

The anti-bacterial compounds and methods of the present disclosure can have various advantageous properties and applications. For instance, in some embodiments, the anti-bacterial compounds of the present disclosure possess broad-spectrum anti-$Gram^+$ activity. In some embodiments, the anti-bacterial compounds of the present disclosure inhibit the growth and proliferation of bacteria, for example, but not limited to, $Gram^+$ bacteria and antibiotic resistant $Gram^+$ bacteria.

In some embodiments, the anti-bacterial compounds of the present disclosure have potent antibacterial activity. In some embodiments, the anti-bacterial compounds of the present disclosure enhance the activity of various active agents, such as, for example, oxacillin. In some embodiments, the anti-bacterial compounds of the present disclosure provide for synergy with oxacillin or other active agents.

In some embodiments, the anti-bacterial compounds of the present disclosure can have one or more of the following advantages: (i) the anti-bacterial compounds of the present disclosure provide good solubility; (ii) the anti-bacterial compounds of the present disclosure have intrinsic anti-bacterial activity toward MRSA or other bacterial strains; (iii) the anti-bacterial compounds of the present disclosure provide for sensitizing MRSA to second-generation penicillin; (iv) the anti-bacterial compounds of the present disclosure can have no more than a 4-fold shift in activity upon addition of serum; (v) the anti-bacterial compounds of the present disclosure exhibit no cytotoxicity with towards numerous eukaryotic cells (e.g., Vero cells and other proxy cell systems including, but not limited to, red blood cells); and (vi) the anti-bacterial compounds of the present disclosure exhibit optimal microsomal stability.

Additionally, the anti-bacterial compounds of the present disclosure are rapidly bactericidal, do not select for resistance, and selectively disrupt bacterial membranes over eukaryotic membranes. Furthermore, the anti-bacterial compounds of the present disclosure are non-toxic and display high therapeutic indexes, are devoid of hemolytic activity, and have attractive physicochemical properties that demonstrate anti-bacterial scaffolding for the treatment of $Gram^+$ bacterial infections and antibiotic resistant $Gram^+$ bacterial infections.

ADDITIONAL EMBODIMENTS

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1. Development and Characterization of Potent Membrane Disrupting Agents to Combat Antibacterial Resistant Gram-Positive Bacteria This Example describes the development and characterization of potent membrane disrupting agents to combat antibacterial resistant gram-positive bacteria. In particular, Applicants describe in this Example efforts leading to the identification of 5-aminoquinolone 123 with exceptionally potent gram-positive activity with minimum inhibitory concentrations (MICs) (i.e., ≤0.06 μg/mL) against numerous clinical methicillin-resistant *Staphylococcus aureus* (MRSA) isolates.

Preliminary mechanism of action and resistance studies demonstrate that the 5-aminoquinolones are rapidly bactericidal, do not select for resistance, and selectively disrupt bacterial membranes over eukaryotic membranes. The lead compound is non-toxic, displaying a therapeutic index of greater than 1000, is devoid of hemolytic activity, and has attractive physicochemical properties (c Log P=1.7, MW=391) that warrant further investigation of this promising antibacterial scaffold for treatment of gram-positive infections.

Example 1.1. Introduction

Rising antimicrobial resistance (AMR) threatens global public health, and if unabated, a 'pre-antibiotic era' when infectious diseases caused nearly one-third of all reported deaths may return. The gram-positive bacterium methicillin-resistant *Staphylococcus aureus* (MRSA) is a prototypical multidrug-resistant organism listed by the Centers for Disease Control (CDC) as a top priority pathogen. *S. aureus* is both a commensal microbe found in the nasal mucosa of ~30% of healthy adults and a human pathogen. Infections with *S. aureus* typically occur in immunocompromised individuals with underlying diseases—such as diabetes, acquired immunodeficiency syndrome or loss of neutrophil function—following disruption of the host's cutaneous or mucosal barriers. Disruption of these barriers can be caused by injury, surgical procedures, medical devices, and drug use which can lead to a litany of symptoms, including sepsis, severe skin infections, catheter-associated urinary tract infections and pneumonia.

In 2017 alone, severe cases of MRSA led to an estimated 119,000 systemic infections with a mortality rate of 17%. While MRSA has historically been recognized for its role in healthcare-associated (HA) infections, community-associated (CA) infections have become more prevalent in the past 40 years and often coincide with worse health outcomes.

MRSA was first reported in 1961, only one year after the introduction of the anti-staphylococcal penicillin known as methicillin into clinical practice. β-Lactam resistance in MRSA is due to expression of the altered penicillin-binding protein PBP2a, which is only weakly inhibited by virtually all β-lactam antibiotics. PBP2a is encoded by mecA or similar homologues that are part of a mobile genetic element called the staphylococcal cassette chromosome mec (SCCmec), which can be further classified into fourteen types (I-XIV). SCCmec types I, II, and III are commonly found in healthcare-associated MRSA (HA-MRSA) while SCCmec IV and V are found in both HA-MRSA and community-associated MRSA (CA-MRSA). The different SCCmec types contain other genetic elements that confer resistance to many classes of antibacterial drugs such as tetracyclines, glycopeptides, lipopeptides, macrolides, and aminoglycosides.

Despite the growing rise of antimicrobial resistance, there have only been six new first-in-class antibacterial drugs approved in the past 20 years. Clinicians continue to rely almost exclusively on intravenously administered vancomycin for treatment of hospitalized patients with serious MRSA infections while intravenous daptomycin is used for MRSA bacteremia and endocarditis. Linezolid is an attractive oral switch therapy for MRSA infections and is widely used for treatment of pneumonia and skin and soft tissue infections. Resistance to all three agents has been reported. The limited treatment options, inadequate number of antibacterial agents in the drug pipeline, and emerging resistance to standard-of-care treatment options all point to the need for novel therapeutics with unconventional mechanisms of action.

The bacterial membrane has traditionally been overlooked in antibacterial drug research because membrane-targeting agents are generally considered poorly selective. However, selectivity can be achieved by binding prokaryotic structural lipids, membrane proteins, and cell wall components enabling discrimination from host cell membranes.

Figure 2:
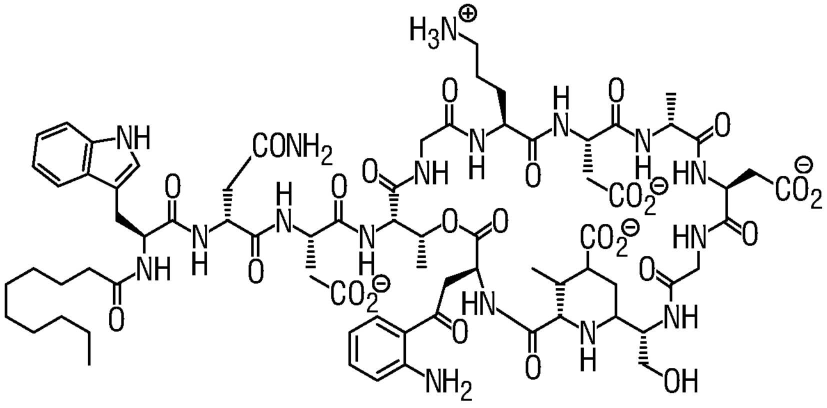
FIG. 2 illustrates therapeutic and experimental membrane-disrupting agents. Daptomycin is a Food and Drug Administration (FDA)-approved antibiotic for treatment of gram-positive bacteria that inserts into the cytoplasmic membrane of the bacteria and permeabilizes it via membrane-associated oligomers. Guavanin 2 is a cationic antimicrobial peptide (CAMP) that disrupts membranes of bacteria via membrane hyperpolarization. The Guavanin 2 structure is taken from PDB 5V1E. Polymyxin $B_1$ is part of the polymyxin class of antibiotics and is an FDA-approved antibiotic that disrupts membranes of gram-positive bacteria.
Figure 2:
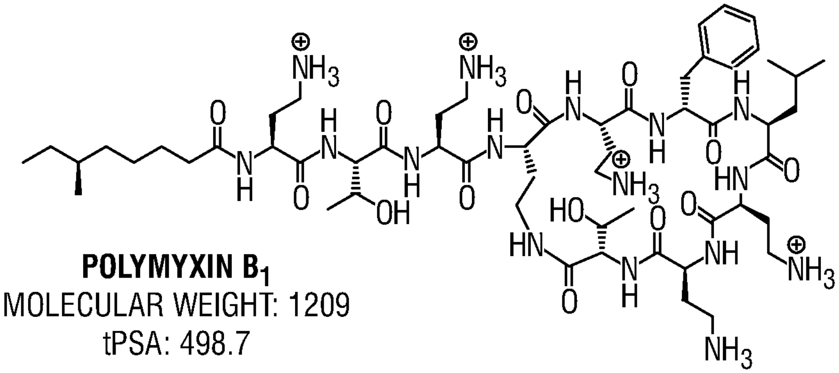
Figure 2:
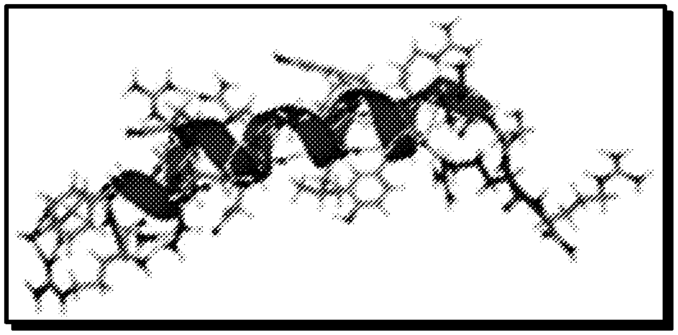
Figure 2:
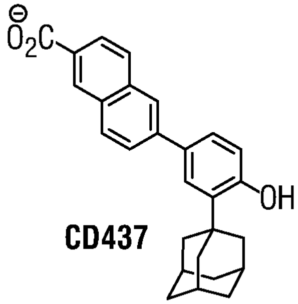
Figure 2:
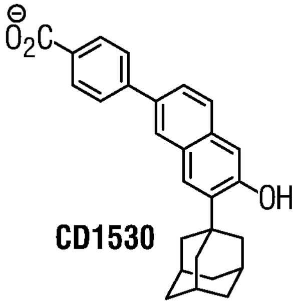

Bacterial membranes represent particularly promising antibacterial targets since they are essential under replicating and non-replicating conditions as well as in planktonic and biofilm cultures. Moreover, the development of resistance to compounds targeting the bacterial membrane is more difficult than to classical antibiotics against easily mutable proteins. The naturally occurring cationic antimicrobial peptides (CAMPs) that disrupt bacterial membranes are part of prokaryotes' and eukaryotes' innate immune system while several classes of Federal Drug Administration (FDA)-approved antibiotics exert their activity through bacterial membrane disruption including the polymyxins, bacitracins, lipopeptides, and lipoglycopeptides (FIG. 2).

The potent antibacterial activity of the synthetic retinoids CD437 and CD1530 (FIG. 2) was recently shown to be caused by membrane disruption as the primary mechanism of action. These aforementioned membrane-targeting antibacterial agents are noted for their poor pharmacokinetic behavior and/or toxicity which emanates from their amphipathic nature and undesirable physicochemical properties. Herein, Applicants report their investigation of a membrane-disrupting aminoquinoline antibacterial scaffold that led to the identification of a highly potent and selective gram-positive antibacterial agent with attractive physicochemical properties.

Example 1.2. Design and Synthesis of Anti-MRSA Compounds

Figure 3:
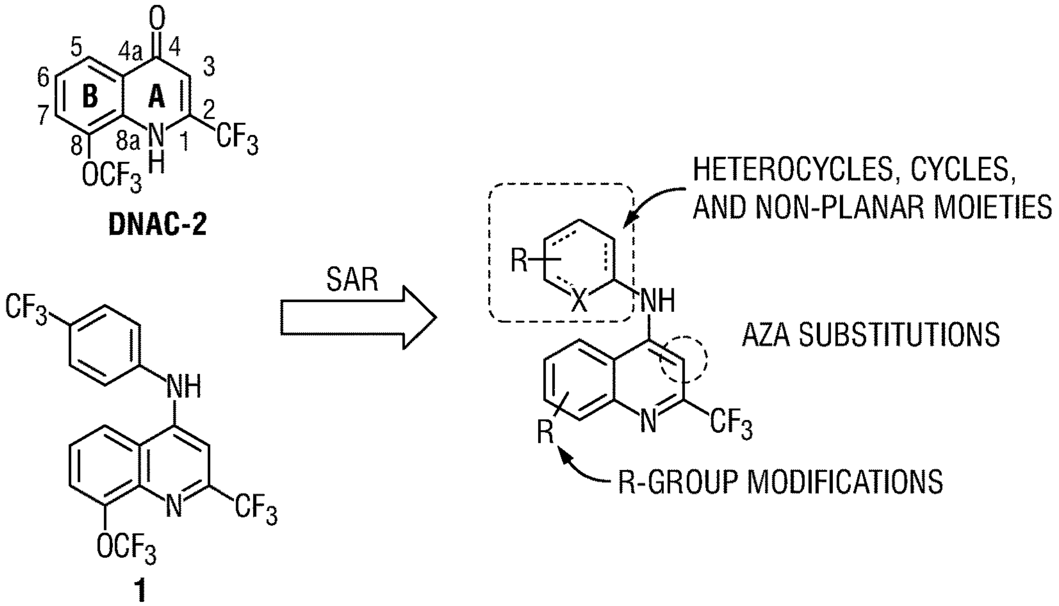
FIG. 3 illustrates high throughput screen (HTS) hits and structure-activity relationships (SAR) analysis of a 4-aminoquinoline scaffold.

Applicants previously reported the identification of the 4-quinolinol derivative DNAC-2 from a high-throughput screening (HTS) campaign with moderate activity (MIC=8 μg/mL) against MRSA (FIG. 3). Intriguingly, DNAC-2 was found to target the membrane of gram-positive bacteria resulting in partial membrane depolarization while displaying no toxicity towards eukaryotic membranes. In addition to DNAC-2, a few other substituted quinolines were identified with the same mechanism of action typified by quinoline 1 (FIG. 3) indicating flexibility at the 4-position. Applicants were attracted to the 4-substituted quinoline scaffold based on its promising activity, chemical tractability for analog synthesis, and prevalence in several approved drugs. Applicants initially sought to examine the structure-activity relationships (SAR) of 1 through substitution and replacement of the 4-aryl ring with more polar and non-planar substituents (FIG. 3). In parallel, Applicants wanted to explore modification and substitution to the quinoline heterocycle through introduction of nitrogen atoms and introduction of more polar substituents at the 2-, 7- and 8-positions to decrease the lipophilicity.

Example 1.3. Chemistry

The first series of quinoline analogues were synthesized from a common set of quinolone building blocks 2-10 that were prepared via a modified Conrad-Limpach reaction between substituted aniline derivatives and 4,4,4-trifluoroacetoacetate in neat polyphosphoric acid (PPA) at 120° C. Meta-substituted anilines typically formed a mixture of both the 5- and 7-regioisomers that were challenging to separate and led to reduced isolated yields of the desired 7-regioisomers, whereas ortho-substituted anilines exclusively afforded the 8-regioisomeric products. The quinolones were evaluated for antibacterial activity and only compounds 3-6 and 10 (DNAC-2 is the same as 6) were found to be active (Table 1). Consequently, only these compounds were derivatized by introduction of a substituent at the 4-position. Quinolone 3 was converted to the corresponding triflate 3a employing triflic anhydride and reacted with various amines and phenols by nucleophilic aromatic substitution ($S_NAr$) to afford 13, 15-22, 25-29, 44, 53-54, 59-62, and 80-83. This strategy proved less effective for electron-deficient amines as well as quinolones with electron donating substituents. In these cases, Applicants utilized a complimentary route by conversion of quinolones to the corresponding aryl chloride or aryl bromides 3b-6b and 10b followed by Buchwald-Hartwig amination to provide 2, 12, 14, 23-24, 30-38, 42-43, 45-51, 55-58, 63-64 and 84.

Scheme 2. 4-Aminoquinoline Synthesis.

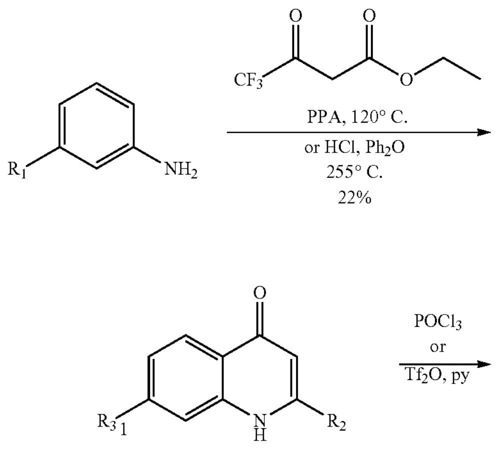

66: $R_1 = SO_2NMe_2$, $R_2 = CF_3$
67: $R_1 = CF_3$, $R_2 = CF_2H$

Scheme 1. 4-Aminoquinoline and 4-oxyquinoline Synthesis.

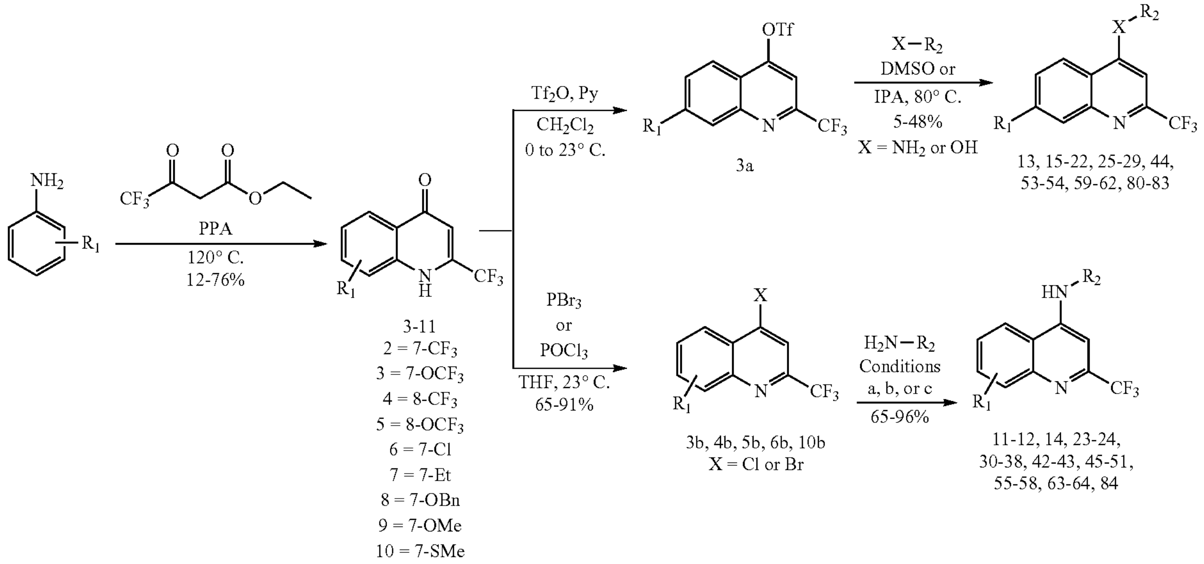

Conditions: [a]$K_3PO_4$/SPhos; $Pd_2(dba)_3 \cdot CH_2Cl_2$, THF, 55° C.; [b]t-BuONa, DPPF, $Pd(dppf)Cl_2 \cdot CH_2Cl_2$, THF, 55° C.; and [c]t-BuONa, XantPhos, $Pd_2(dba)_3$, dioxane 80° C.

Compounds containing a difluoromethyl C-2 substituent were prepared analogously by Conrad-Limpach reaction between 3-trifluoromethylaniline and 4,4-difluoroacetoacetate to afford quinolone 67, which was activated by triflic anhydride to 67a and elaborated to 68 and 69 by $S_NAr$ substitution with 3,4-dichloroaniline and 3-trifluormethoxyaniline, respectively (Scheme 2). Analogs containing a dimethylaminosulfonyl C-7 substituent could not be synthesized using the usual PPA-mediated procedure and required substantially more thermal energy. Compound 66 was instead prepared by refluxing 3-(dimethylaminosulfonyl)aniline and 4,4,4-trifluoroacetoacetate at 255° C. in diphenyl ether (Scheme 2). Chlorination of 66 with $POCl_3$ yielded 66a that was diversified to 39-41 by Buchwald-Hartwig amination.

-continued

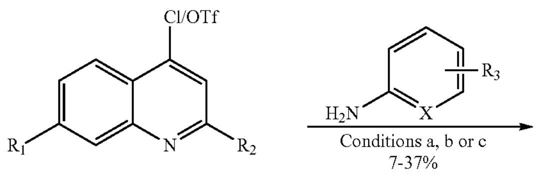

66a - 67a
66a: $R_1$ = -$SO_2NMe_2$, $R_2 = CF_3$
67a: $R_1$ = -$CF_3$, $R_2 = CF_2H$

-continued

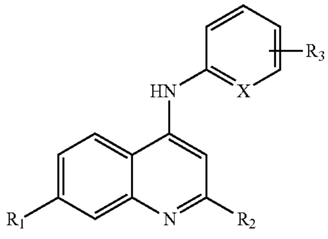

39-41, 68, 69

Conditions: [a]DMSO, 80° C.; and [b]HCl, EtOH, reflux [c]$PD_2(dba)_3$, XantPhos, t-BuONa, dioxane 80° C.

Applicants synthesized a series of mono-, di- and trifluorinated analogs of the B-ring in an attempt to replace the lipophilic C-7 trifluoromethyl group. While m-fluoroaniline reacted with 4,4,4-trifluoroacetoacetate in neat polyphosphoric acid (PPA) at 100° C. to furnish 70, the di- and tri-fluoroanilines required heating at 150° C. to effect cyclization to quinolones 71-73 (Scheme 3). Halogenation of 70-73 to quinolines 70a-73a followed by Buchwald-Hartwig amination as described previously yielded 74-79.

Scheme 3. Synthesis of Fluorinated B-Ring Analogues.

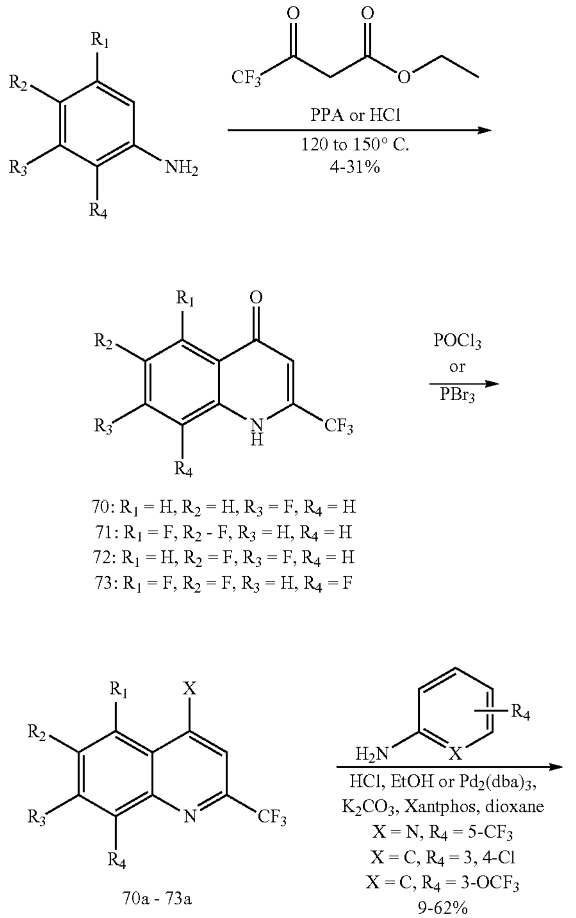

70: $R_1$ = H, $R_2$ = H, $R_3$ = F, $R_4$ = H
71: $R_1$ = F, $R_2$ - F, $R_3$ = H, $R_4$ = H
72: $R_1$ = H, $R_2$ = F, $R_3$ = F, $R_4$ = H
73: $R_1$ = F, $R_2$ = F, $R_3$ = H, $R_4$ = F

70a - 73a

-continued

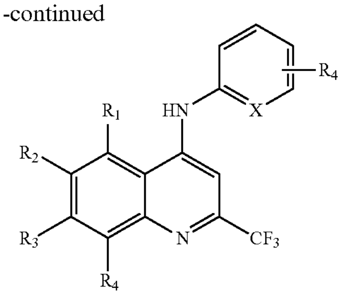

74-79

In an attempt to reduce the lipophilicity of the aminoquinolines, Applicants targeted the synthesis of quinazolines containing an additional nitrogen atom in the A-ring. Synthesis commenced from commercially available 2-amino-4-(trifluoromethyl)benzonitrile that was oxidized from the nitrile to the amide intermediate 86 by treatment with an alkaline solution of hydrogen peroxide (Scheme 4). Treatment of the resulting substituted aniline 86 with 2,2,2-trifluoroacetyl chloride furnished the bis-amide intermediate 87, which was cyclized to the quinazolone 88 employing potassium hydroxide in ethanol at reflux. Chlorination of quinazolone 88 with thionyl chloride in DMF followed by $S_NAr$ substitution with 3,4-dichloroaniline, 3-trifluoromethoxyaniline, and 2-amino-5-trifluoromethylpyridine afforded the final 4-aminoquinazolines 89-91.

Scheme 4. Synthesis of 4-Aminoquinazolines.

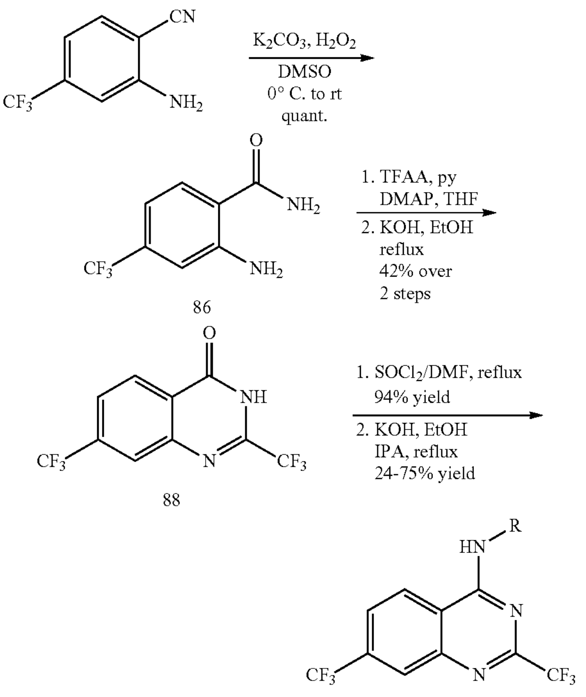

86

88

89-91

The pyrido[2,3-d]pyrimidine scaffold containing two additional nitrogen atoms was investigated as a quinoline isostere in an attempt to further decrease lipophilicity. The synthesis began by $S_NAr$ substitution of 2-chloro-3-cyano-6-trifluoromethylpyridine with ammonia in THF followed by base-promoted hydration of the cyano group to furnish amide 92 (Scheme 5). Subsequent condensation of 92 with ethyl trifluoroacetate and base-catalyzed annulation afforded an intermediate pyrido[2,3-d]pyrimidin-4-one derivative that was converted to 93 by $POCl_3$ mediated chlorination. $S_NAr$ substitution of 93 with 3,4-dichloroaniline yielded 94 while reaction of 93 with 2-amino-5-trifluoromethylpyridine to provide 95 required the complimentary Buchwald-Hartwig amination.

Scheme 5. Synthesis of Pyrido[2,3-d]pyrimidines.

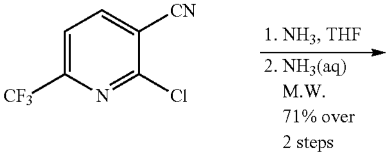

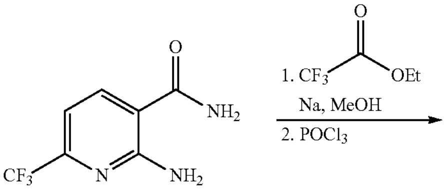

92

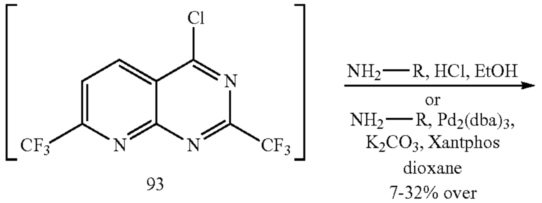

93

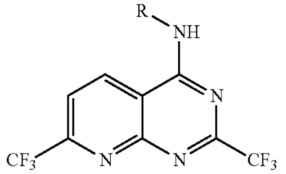

94: R = 3,4-difluorophenyl
95: R = 5-(trifluoromethyl)-pyridin-2-yl

The cinnoline analogs were the final set of aza-analogs of the quinoline scaffold prepared. Synthesis of the requisite cinnoline-4-one building block was achieved by diazotization of 2-amino-4-trifluoromethylacetophenone 96 with sodium nitrite and aqueous hydrogen chloride. Following removal of the solvents in vacuo, the resultant diazonium ion was directly treated with sodium acetate at 100° C. to afford 97 (Scheme 6). The cinnoline-4-one intermediate 97 was then activated with phosphorus oxychloride and coupled to 3,4-difluoroaniline and 2-amino-5-trifluoromethylpyridine by $S_NAr$ substitution and Buchwald-Hartwig reaction to provide 98 and 99, respectively.

Scheme 6. Cinnoline Synthesis.

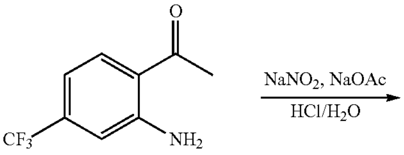

96

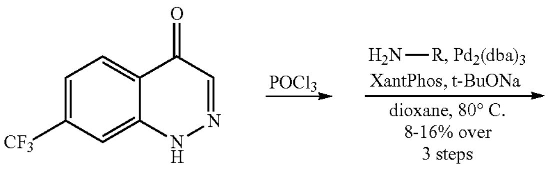

97

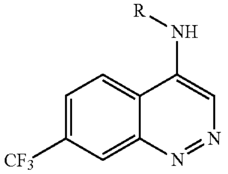

98: R = 3,4-difluorophenyl
99: R = 5-(trifluoromethylpyridin-2-yl

Applicants developed an alternate quinoline synthesis to explore modification of the C-2 position featuring a 2,4-dichloroquinoline intermediate. This was accomplished by intramolecular Claisen-like condensation of ethyl N-acetyl-2-amino-4-trifluoromethylbenzoate mediated by potassium bis(trimethylsilyl)amide (KHMDS) to afford a 4-hydroxy-quinoline-(2H)-one intermediate, which was converted to 2,4-dichloroquinoline 100 by refluxing in phosphorus oxychloride. $S_NAr$ substitution by Boc-protected piperazine gave 101 along with the C-4 regioisomer (not shown). Buchwald-Hartwig coupling of 101 and 2-amino-5-trifluoromethylpyridine followed by TFA deprotection of the Boc group gave the desired analogue 102. The regioisomeric analog 103 was prepared from the corresponding C-4 piperazine intermediate isolated as a side-product in the preparation of 101. The C-2 and C-4 morpholino substituted analogues 104 and 105 were synthesized in an analogous fashion.

Scheme 7. Synthesis of a C-2 Piperazine Analogue.

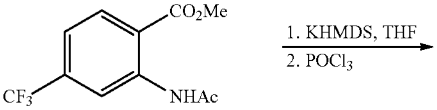

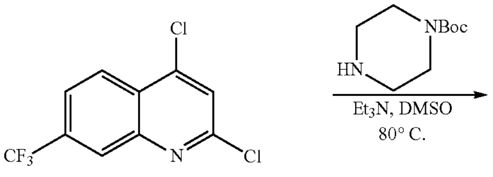

100

-continued

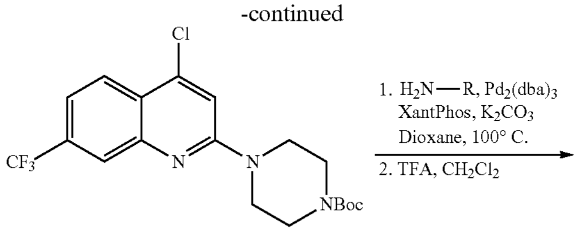

101

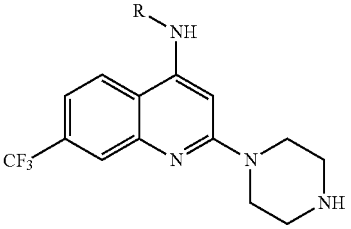

102: R = 5-(trifluoromethyl)-pyridin-2-yl

Applicants next conceived of a hybrid scaffold of the initial active quinoline-4-ones and the aryl-substituted 4-aminoquinolines, giving an aryl-substituted 5-aminoquinoline-4-ones scaffold (Scheme 8). The two-step synthesis started from condensation of 3-bromo-5-trifluoromethylaniline and ethyl 2,2,2-trifluoromethylacetoacetate in neat PPA to give two separable regioisomers 106 and 107. The structure of the regioisomers were assigned by $^1H$ NMR analysis of the debrominated products generated by palladium-catalyzed dehalogenation (not shown). Following optimization of the Buchwald-Hartwig amination conditions, Applicants were able to access the desired C-5 substituted aminoquinoline-4-ones 108-118 from 106. The corresponding C-7 substituted aminoquinoline-4-ones 119-122 were prepared from 107. The C-7 fluoro derivative 123 was synthesized analogously from 3-bromo-5-fluoroaniline.

Based on the promising activity of quinolin-4-one 111, but low solubility (Table 8), Applicants sought to prepare an alkoxycarbonate prodrug for in vivo studies to increase solubility and bioavailability based on the precedent of previous literature, which successfully applied this strategy in preclinical development of novel antimalarial quinolone ELQ-330. Direct installation of the promoiety onto 111 was unsuccessful; however, the alkoxycarbonate promoiety could be introduced in onto 5-bromoquinoline 106 by cesium carbonate mediated alkylation of chloromethyl ethyl carbonate in acetone. The resulting methyloxycarbonate ester 124 was then converted to the desired final product 125 via a Buchwald-Hartwig amination with 2-amino-5-trifluoromethylpyridine.

Scheme 9. Prodrug Synthesis.

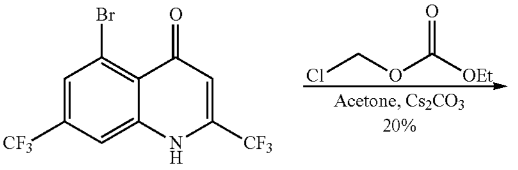

106

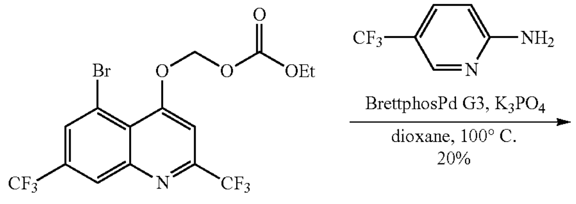

124

Scheme 8: C-5 and C-7 Substituted Quinoline-4-ones.

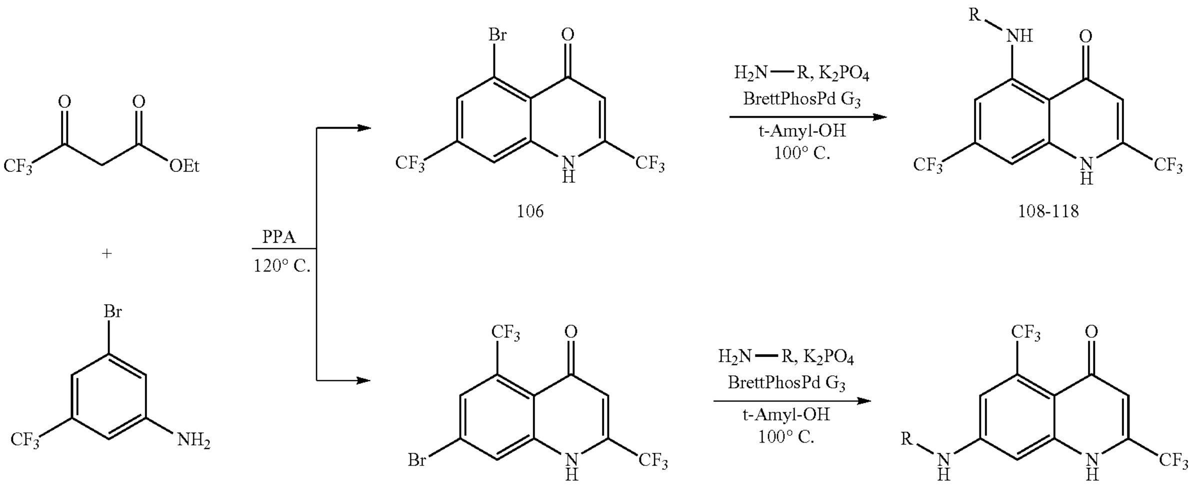

106

108-118

107

119-122

-continued

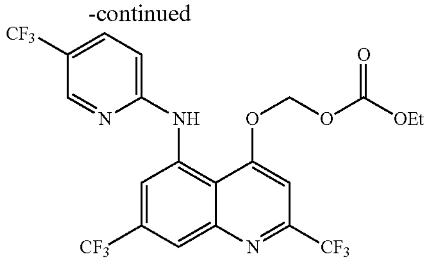

125

Example 1.4. Microbiology

The antibacterial activity of compounds was initially determined against a clinical strain of methicillin-resistant *S. aureus* (FPR3757) in Muellar-Hinton (MH) broth according to CLSI guidelines to determine the minimum inhibitory concentration (MIC) that resulted in complete inhibition of observable growth. The first set of compounds evaluated were analogs at the C-7 and C-8 positions of the initial quinolone hit DNAC-2 since the other HTS hits identified (data not shown) were substituted at these positions (Table 1). Applicants first explored modification at the C-7 position with a small series of electron-donating and withdrawing substituents. The trifluoromethyl 2 and trifluoromethoxy 3 are the most potent with MICs of 4-8 µg/mL while chloro 6 is slightly weaker with an MIC of 20 µg/mL. However, analogs containing electron donating groups at C-7 including ethyl 7, benzyloxy 8, methoxy 9 and methylthio 10 are weakly active displaying MICs of 320-640 µg/mL indicating electron-donating substituents at C-7 are poorly tolerated. The impact of electronics is best illustrated with methoxy 9, which is 80-160 less potent that the isosteric trifluoromethoxy 3. The C-8 position was evaluated with trifluoromethyl 4 and trifluoromethoxy 5 containing the optimal C-7 substituents. Both 4 and 5 are equipotent to the corresponding C-7 analogs 2 and 3 indicating some flexibility of the quinolone scaffold.

TABLE 1

Substituted Quinoline-4-one Analogues.

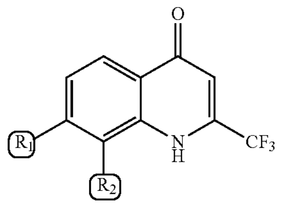

| Compound | $R_1$ | $R_2$ | MIC µg/mL | cLogP |
|---|---|---|---|---|
| 2 | $CF_3$ | H | 5 | 2.2 |
| 3 | $OCF_3$ | H | 4-8 | 2.4 |
| 4 | H | $CF_3$ | 2-4 | 2.2 |
| 5 | H | $OCF_3$ | 5 | 2.4 |
| 6 | chloro | H | 20 | 2.0 |
| 7 | ethyl | H | 320 | 2.3 |
| 8 | benzylether | H | 640 | 3.1 |
| 9 | methoxy | H | 640 | 1.3 |
| 10 | thiomethyl | H | 640 | 1.9 |

Applicants next explored the SAR of the C-4 aryl substituent of 4-aminoquinoline 1 whose MIC is 8 µg/mL (Table 2). Applicants' first series of compounds contain a 7-trifluoromethyl rather than the 8-trifluoromethoxy substituent found in 1. The 2'-, 3'-, and 4'-chlorophenyl analogs 15-17 helped to define the steric requirements for activity: 2'-chlorophenyl 15 is inactive while both 3'-chlorophenyl 16 and 4'-chlorophenyl 17 possess MICs of 0.125-0.25 µg/mL, which represents a dramatic 32-64-fold increase in potency over 1. Given the enhanced potency of the chloro-substituted analogs, Applicants conducted a halogen scan and evaluated 3'-fluorophenyl 18, 3'-bromophenyl 19 and 3'-iodophenyl 20. The more lipophilic halogens 19 and 20 maintain potent activity with MICs of 0.25 µg/mL while the fluoro analog has a substantial 16-64-fold loss of potency. Applicants also explored a couple of 3',4'-disubstituted analogs with 3',4'-fluorophenyl 21 and 3',4'-dichlorophenyl 22. Both analogs display further improvements in potency relative to the corresponding mono-halogenated analogs and the MIC of 3',4'-dichlorophenyl 22 decreased to 0.0625 µg/mL, the lowest value among the series of analogs described in Table 2. Additionally, a broader array of substituents were explored at the 3'- and 4'-positions of the aryl ring including phenyl 11, 3'-acetyl 13, 3'-cyanophenyl 14, 3'-hydroxymethylphenyl 23, 3'-methylthiophenyl 24, 3'-methoxyphenyl 25, 3'-trifluoromethylphenyl 26, 3'-trifluoromethoxyphenyl 27, 3'-(morpholino)phenyl 29, 4'-(morpholino)phenyl 30 and 3',4'-(methylenedioxy)phenyl 28. Analogs containing polar acetyl, cyano, methoxy, hydroxymethyl, methylenedioxy, and morpholino substituents are inactive or weakly active with MICs generally >16 µg/mL. By contrast, analogs containing lipophilic groups including methylthio and trifluoromethyl are potent with MICs of 0.25-0.50 µg/mL, the exception being trifluoromethoxy 27, whose MIC is 8 µg/mL. In an attempt to decrease the lipophilicity, Applicants replaced the phenyl ring of 3'-trifluoromethylphenyl 26 by a pyridine to furnish 5'-(trifluoromethyl)pyridin-2-yl 31, which fortuitously maintains activity providing an identical MIC to 26 while decreasing the calculated log P by 1.2 units to 6.0. While introduction of an appropriately substituted arylamino group led to a substantial enhancement in activity relative to the simple quinolones shown in Table 1, this boost in potency came at the expense of substantially increased lipophilicity. This is exemplified by 3'-trifluoromethylphenyl 26 whose 16-fold improvement in potency relative to the parent quinolone 3 is offset by a 5.1 unit increase in the calculated log P. Attempts to decrease lipophilicity by introduction of polar substituents onto the aryl ring led to sharp reductions in potency. However, heterocyclic replacement of the phenyl ring by a pyridine is tolerated providing a means to partially address the increased lipophilicity of the N-(arylamino) quinolines.

The SAR of the N-(arylamino)quinoline scaffold was further probed at the C-7 and C-8 positions with 7-methoxy, 7-trifluoromethoxy, 7-(dimethylamino)sulfonyl, 8-trifluoromethyl, and 8-trifluoromethoxy substituents with the C-4 aryl moiety selected from representatives of 12-31 including 3',4'-difluorophenyl 21 (MIC of 0.125-0.25 µg/mL), 3',4'-dichlorophenyl 22 (MIC of 0.0625 µg/mL), 3'-(trifluoromethoxy)phenyl 27 (MIC of 8 µg/mL), and 5'-(trifluoromethyl)pyridin-2-yl 31 (MIC of 0.25 µg/mL). Replacement of the C-7 trifluoromethyl group by a trifluoromethoxy group in 32-34 yielded flat SAR with MICs ranging from 0.5-1 µg/mL. The SAR trend from this limited set of compounds did not parallel the SAR observed with the 7-trifluoromethyl series of compounds. The isosteric 7-methoxy analogs 35-38 were largely inactive (MICs of >32 µg/mL), a result consistent with the quinolone SAR described in Table 1. The observation that electron-withdrawing substituents at C-7 are favorable prompted exploration of the 7-dimethylaminosulfonyl group with 39-41 since sulfonamides are electron-withdrawing and considerably more polar than a trifluoromethyl group. Unfortunately, this set of compounds was only weakly active with MICs ranging from 8 to >32 μg/mL suggesting optimal quinoline substituents at C-7 should not only be electron-withdrawing, but also nonpolar. Analogs bearing trifluoromethyl and trifluoromethoxy substituents at C-8 exhibited remarkably flat SAR with MICs of 0.5-2.0 μg/mL. The SAR trend was inconsistent with the 7-trifluoromethyl substituted analogs, whose MICs varied over 128-fold for the same set of C-4 aryl substituents. Taken together, the SAR from 32-47 demonstrates substitution at C-7 is preferred and optimal substituents at this position should be non-polar and strongly electron-withdrawing.

TABLE 2

Aryl 4-aminoquinoline Analogues.

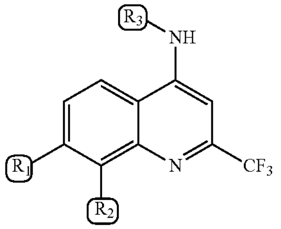

| Compound | $R_1$ | $R_2$ | $R_3$ | MIC μg/mL | cLogP |
|---|---|---|---|---|---|
| 1 | H | $OCF_3$ | 3-(trifluoromethoxy)phenyl | 8 | 7.9 |
| 11 | $CF_3$ | H | phenyl | 128 | 6.4 |
| 12 | $CF_3$ | H | 2-isopropylphenyl | 320 | 7.8 |
| 13 | $CF_3$ | H | 3-acetylphenyl | >128 | 5.9 |
| 14 | $CF_3$ | H | 3-benzonitrile | >32 | 5.9 |
| 15 | $CF_3$ | H | 2-chlorophenyl | >16 | 7.1 |
| 16 | $CF_3$ | H | 3-chlorophenyl | 0.25 | 7.1 |
| 17 | $CF_3$ | H | 4-chlorophenyl | 0.12 | 7.1 |
| 18 | $CF_3$ | H | 3-fluorophenyl | 4-16 | 6.5 |
| 19 | $CF_3$ | H | 3-bromophenyl | 0.25 | 7.3 |
| 20 | $CF_3$ | H | 3-iodophenyl | 0.25 | 7.5 |
| 21 | $CF_3$ | H | 3,4-difluorophenyl | 0.12-0.25 | 6.6 |
| 22 | $CF_3$ | H | 3,4-dichlorophenyl | 0.06 | 7.7 |
| 23 | $CF_3$ | H | 3-(hydroxymethyl)phenyl | >16 | 5.3 |
| 24 | $CF_3$ | H | 3-thiomethylphenyl | 0.25-0.5 | 7.0 |
| 25 | $CF_3$ | H | 3-methoxyphenyl | >64 | 6.3 |
| 26 | $CF_3$ | H | 3-(trifluoromethyl)phenyl | 0.25 | 7.3 |
| 27 | $CF_3$ | H | 3-(trifluoromethoxy)phenyl | 8 | 7.4 |
| 28 | $CF_3$ | H | 3,4-(methylenedioxy)phenyl | >4 | 6.2 |
| 29 | $CF_3$ | H | 3-(morpholino)phenyl | >16 | 5.8 |
| 30 | $CF_3$ | H | 4-(morpholino)phenyl | >16 | 5.8 |
| 31 | $CF_3$ | H | 5-(trifluoromethyl)pyridin-2-yl | 0.25 | 6.1 |
| 32 | $OCF_3$ | H | 3,4-dichlorophenyl | 0.5-1 | 8.2 |
| 33 | $OCF_3$ | H | 3-(trifluoromethoxy)phenyl | 1 | 7.9 |
| 34 | $OCF_3$ | H | 5-(trifluoromethyl)pyridin-2-yl | 1 | 6.5 |
| 35 | OMe | H | 3,4-dichlorophenyl | 2 | 6.0 |
| 36 | OMe | H | 3,4-difluorophenyl | >32 | 4.9 |
| 37 | OMe | H | 3-(trifluoromethoxy)phenyl | >32 | 5.7 |
| 38 | OMe | H | 5-(trifluoromethyl)pyridin-2-yl | 32 | 4.3 |
| 39 | $S(O)_2N(Me$ | H | 3,4-difluorophenyl | >32 | 5.1 |
| 40 | $S(O)_2N(Me$ | H | 3-(trifluoromethoxy)phenyl | 8 | 5.9 |
| 41 | $S(O)_2N(Me$ | H | 5-(trifluoromethyl)pyridin-2-yl | 8 | 4.5 |
| 42 | H | $OCF_3$ | 3,4-dichlorophenyl | 0.5 | 8.2 |
| 43 | H | $OCF_3$ | 3-(trifluoromethoxy)phenyl | 1 | 7.8 |
| 44 | H | $OCF_3$ | 5-(trifluoromethyl)pyridin-2-yl | 1 | 6.5 |
| 45 | H | $CF_3$ | 3,4-dichlorophenyl | 0.5-2 | 8.2 |
| 46 | H | $CF_3$ | 3-(trifluoromethyl)phenyl | 1 | 7.9 |
| 47 | H | $CF_3$ | 5-(trifluoromethyl)pyridin-2-yl | 0.5 | 6.5 |

The promising activity of compound 31 containing a 5'-(trifluoromethyl)pyridin-2-yl-amino moiety appended to C-4 of the quinoline prompted Applicants to explore more diverse heterocyclic substituents at C-4 (Table 3). A primary objective in these analogues was to decrease the overall lipophilicity through introduction of polar atoms and to reduce the planarity by increasing the $sp^3$ character since lipophilic and planar molecules tend to have poor solubility that adversely impacts drug disposition properties. Replacement of the 5'-(trifluoromethyl)pyridin-3-yl-amino group at C-4 with a closely related 4'-(chloro)pyridin-2-yl-amino group in 48 led to an 8-fold loss of activity while transposition of the pyridine nitrogen by one atom in 2'-(trifluoromethyl)pyridin-5-yl-amino 49 completely abolished activity. These findings foreshadowed Applicants' unsuccessful attempts to modify the C-4 substituent. Thus pyridones 50-52, pyridine 53, picolinate 54, pyrimidine 56, cyclohexane 57, hydroxypiperidine 58, morpholine 59, aminomethylpyrrolidine 60, indazole 61, isoindole 62, pyrrolopyridine 63, indolone 64 and azabicyclooctanol 65 were inactive at the highest concentration evaluated (MIC>32 μg/mL). Only, aminothiazole 55 demonstrated moderate activity with an MIC of 2 μg/mL.

TABLE 3

Heterocyclic 4-substitutions.

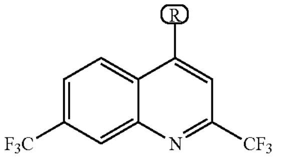

| Compound | R | MIC μg/mL | cLogP |
|---|---|---|---|
| 31 | 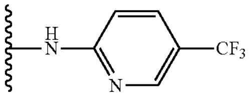 [SMILES: *Nc1ccc(C(F)(F)F)cn1] | 0.25 | 6.0 |
| 48 | 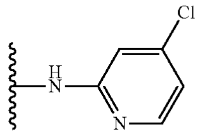 | 2 | 5.8 |
| 49 | 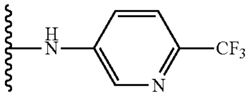 | >32 | 6.0 |
| 50 | 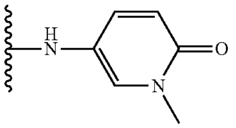 [SMILES: *Nc1ccc(=O)n(C)c1] | >32 | 4.2 |
| 51 | 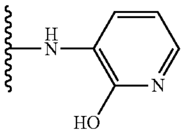 [SMILES: *Nc1cccnc1O] | >128 | 5.4 |
| 52 | 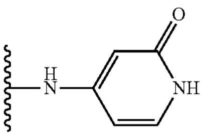 [SMILES: *Nc1cc[nH]c(=O)c1] | >32 | 3.7 |
| 53 | 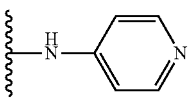 [SMILES: *Nc1ccncc1] | >32 | 5.1 |
| 54 | 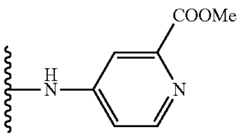 [SMILES: *Nc1ccnc(C(=O)OC)c1] | >32 | 4.7 |
| 55 | 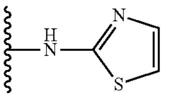 | 1-2 | 4.9 |

TABLE 3-continued

Heterocyclic 4-substitutions.

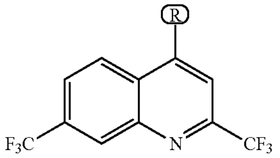

| Compound | R | MIC μg/mL | cLogP |
|---|---|---|---|
| 56 | 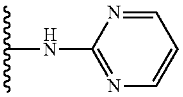 [SMILES: *Nc1ncccn1] | >32 | 4.2 |
| 57 | 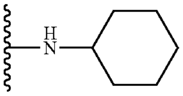 | >16 | 6.6 |
| 58 | 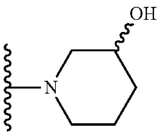 | >32 | 4.0 |
| 59 | 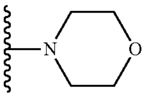 | >32 | 4.0 |
| 60 | 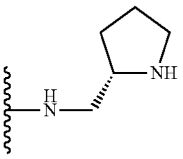 [SMILES: *NC[C@@H]1CCCN1] | >32 | 4.9 |
| 61 | 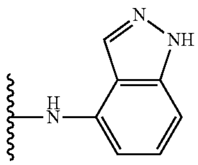 [SMILES: *Nc1cccc2[nH]ncc12] | >32 | 6.0 |
| 62 | 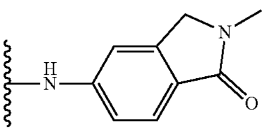 [SMILES: *Nc1ccc2c(c1)CN(C)C2=O] | >32 | 5.2 |
| 63 | 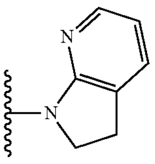 | >32 | 5.3 |

TABLE 3-continued

Heterocyclic 4-substitutions.

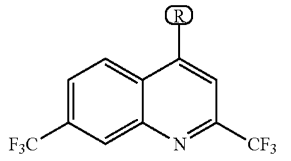

| Compound | R | MIC µg/mL | cLogP |
|---|---|---|---|
| 64 | 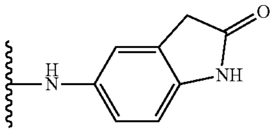 [SMILES: *Nc1ccc2c(c1)CC(=O)N2] | >32 | 5.0 |
| 65 | 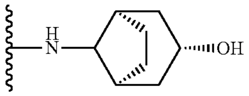 [SMILES: *NC1[C@@H]2CC[C@H]1C[C@@H](O)C2] | >32 | 5.3 |

Further structural modifications were focused on reducing the calculated Log P by modifications of the quinoline core employing the optimal C-4 substituents: 3',4'-dichlorophenyl, 3'-(trifluoromethoxy)phenyl and 5'-(trifluoromethyl) pyridin-2-yl from compounds 22, 27, and 31, respectively. The trifluoromethyl groups at the C-2 and C-7 positions contribute significantly to the overall lipophilicity, thus the next series of analogs explored replacement of the trifluoromethyl group by difluoromethyl and aryl fluorides, which were predicted to lower the log P by approximately 0.7 units per trifluoromethyl group (Table 4). Replacement of the C-2 trifluoromethyl group of 22 with a difluoromethyl group afforded compound 68, which is 16-fold less potent than 22. Conversely, compound 69 exhibits a 16-fold increase in potency relative to the corresponding trifluoromethyl analog 27. Applicants cannot reconcile the disparate impact on potency of the difluoromethyl group based on this limited set of analogs, but the difluoromethyl group appears to level the SAR as both 68 and 69 have similar MICs. Replacement of the C-7 trifluoromethyl group by a fluorine was explored with analogs 74-79. Substitution of the C-7 trifluoromethyl group by a 7-fluoro moiety in 74-76 led to uniform 4-8-fold reductions in potency relative to the corresponding trifluoromethyl analogs 22, 27 and 31 providing MICs ranging from 0.5-2.0 µg/mL. Given the more predictable SAR of the aryl fluoride analogs, Applicants sought to introduce additional fluorine atoms in the B-ring of 76 at the 5, 6, and 8-positions with difluorinated analogs 77-78 and trifluorinated analog 79. While fluorine was poorly tolerated at the 5 and 6-positions, the 6,7-difluoro analog 78 fully regained the activity of the parent trifluoromethyl analog 31. Collectively, these results indicate modest attenuation of the log P can be achieved by replacement of the lipophilic trifluoromethyl groups with fluorine atoms while maintaining potent activity.

TABLE 4

Fluorine Substitutions.

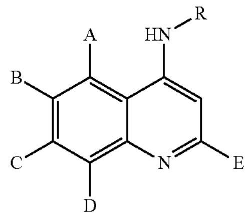

| Compound | A | B | C | D | E | R | MIC µg/mL | cLogP |
|---|---|---|---|---|---|---|---|---|
| 68 | H | H | $CF_3$ | H | $CHF_2$ | 3,4-dichlorophenyl | 1 | 6.3 |
| 69 | H | H | $CF_3$ | H | $CHF_2$ | 3-(trifluoromethoxy)phenyl | 0.5 | 6.6 |
| 74 | H | H | F | H | $CF_3$ | 3,4-dichlorophenyl | 0.5 | 7.0 |
| 75 | H | H | F | H | $CF_3$ | 3-(trifluoromethoxy)phenyl | 2 | 6.7 |
| 76 | H | H | F | H | $CF_3$ | 5-(trifluoromethyl)pyridin-2-yl | 1 | 5.3 |
| 77 | F | F | H | H | $CF_3$ | 5-(trifluoromethyl)pyridin-2-yl | 16-32 | 5.3 |
| 78 | H | F | F | H | $CF_3$ | 5-(trifluoromethyl)pyridin-2-yl | 0.25 | 5.3 |
| 79 | F | F | H | F | $CF_3$ | 5-(trifluoromethyl)pyridin-2-yl | >32 | 5.5 |

With extensive coverage of the C2, C-4, C-7 and C-8 positions of the 4-aminoquinoline, the SAR campaign moved towards heteroatom modifications of the 4-amino-quinoline core. Applicants first studied the importance of the 4-amino group and specifically the importance of an H-bond donor at this position with ether analogues 80-83, N-methyl derivative 84 and amide 85 (Table 5). Compounds 80-85 are inactive with MICs greater than 32 μg/mL indicating an NH moiety is useful for activity and a one atom linker is often preferred. Applicants then explored quinazoline analogs 89-91 containing a single aza substitution at the C-3 position, which retains a similar pharmacophore while lowering the calculated Log P by 1.5 units. The 3',4'-dichlorophenyl 89, and 5'-(trifluoromethyl)pyridin-2-yl 91 quinazoline analogues are 8-fold less active than the parent quinolines 22, 31 while the trifluoromethoxy 90 derivative has an opposite 8-fold increase in potency relative to the parent quinoline 27. The aza substitution thus appears to flatten the SAR as the potency of 89-91 varies only 4-fold from 0.5-2.0 μg/mL. Introduction of another nitrogen atom into the quinazoline at the C-8 position led to pyridopyrimidine derivatives 94-95 and an attendant decrease in log P by almost 3 units. Unfortunately, both pyridopyrimidines 94 and 95 have drastically reduced activity with MICs≥32 μg/mL.

TABLE 5

Heteroatom Exchanges

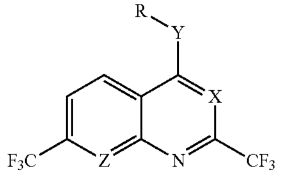

| Compound | X | Y | Z | R | MIC μg/mL | cLogP |
|---|---|---|---|---|---|---|
| 80 | CH | O | CH | 3-chlorophenyl | >32 | 6.8 |
| 81 | CH | O | CH | 3-fluorophenyl | >32 | 6.2 |
| 82 | CH | O | CH | 3,4-dichlorophenyl | >32 | 7.4 |
| 83 | CH | O | CH | 3-(trifluoromethoxy)phenyl | >32 | 7.1 |
| 84 | CH | NMe | CH | 4-trifluoromethylphenyl | >32 | 7.4 |
| 85 | CH | N(C═O) | CH | 5-(trifluoromethyl) pyridin-2-yl | >32 | 5.3 |
| 89 | N | NH | CH | 3,4-dichlorophenyl | 0.5 | 6.9 |
| 90 | N | NH | CH | 3-(trifluoromethoxy)phenyl | 1 | 6.6 |
| 91 | N | NH | CH | 5-(trifluoromethyl) pyridin-2-yl | 2 | 5.1 |
| 94 | N | NH | N | 3,4-difluorophenyl | 32 | 4.0 |
| 95 | N | NH | N | 5-(trifluoromethyl) pyridin-2-yl | >32 | 5.8 |

A few remaining miscellaneous modifications to reduce the log P of the 4-aminoquinoline scaffold are described in Table 6 and Table 7. The cinnoline analogues 98 and 99 lacking a C-2 trifluoromethyl group and containing a nitrogen atom at C-2 are unsurprisingly inactive (Table 6). Remarkably, introduction of a piperazine at C-2 with 102 was reasonably well tolerated yielding an MIC of 0.5-1.0 μg/mL while the morpholine analogue 104 is inactive (Table 7). The piperazine and morpholine constitutional isomers 103-104 have modest activity with MICs of 4-8 μg/mL.

TABLE 6

Cinnoline and Amide Analogues.

| Compound | Core Structure | R | MIC μg/mL |
|---|---|---|---|
| 98 | 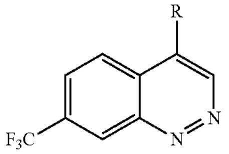 | 3,4-difluoroanilino | >32 |
| 99 | 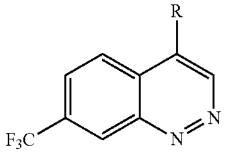 | 5-(trifluoromethyl) pyridin-2-yl-amino | >32 |

TABLE 7

C-2 and C-4 Substituted Quinolines.

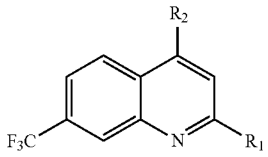

| Compound | $R_1$ | $R_2$ | MIC μg/mL | cLogP |
|---|---|---|---|---|
| 102 | Piperazinyl | 5-(trifluoromethyl) pyridin-2-yl-amino | 0.5-1 | 5.1 |
| 103 | 5-(trifluoromethyl) pyridin-2-yl-amino | piperazinyl | 4-8 | 5.1 |
| 104 | Morpholino | 5-(trifluoromethyl) pyridin-2-yl-amino | >32 | 5.1 |
| 105 | 5-(trifluoromethyl) pyridin-2-yl-amino | morpholino | 8 | 5.1 |

The final series of compounds investigated was a hybrid scaffold of the initial active quinol-4-one (Table 1) and the aryl-substituted 4-aminoquinoline (Table 2) to afford an aryl-substituted 5-aminoquinolin-4-one scaffold (Table 8) in an attempt to lower the calculated log P. All of the 5-aminoquinolin-4-ones 108-123 with the exception of 118 showed good to outstanding antibacterial activity with MICs ranging from <0.06 to 4 μg/mL while simultaneously decreasing the calculated Log P by two and up to five units. The optimal C-4 substituents in the 4-aminoquinoline series yielded extremely potent 5-aminoquinolone analogues 108-111 with MICs less than 0.06 μg/mL and attendant dramatic reductions in lipophilicity. The constitutional isomers 119-123 containing the arylamino substituents at the C-7 rather than the C-5 position found in 108-111 were substantially weaker with MICs ranging from 1-4 μg/mL, representing a 16- to greater than 64-fold loss in potency. Compound 111 was the first potent derivative synthesized with a calculated log P of less than four. Given the impressive activity of 108-111 Applicants sought to further examine closely related substituents containing polar substituents and/or greater sp3 character including 5-fluoropyridin-2-yl-amino 112, 5-dimethylaminopyridin-2-yl-amino 113, 6-(trifluoromethyl)pyridazin-3-yl-amino 114, 3-(N,N-dimethylsulfonamide)pyridine-6-yl-amino 115, 4-amino-1H-indazolyl 116, 4-(trifluoromethyl)cyclohex-1-yl-amino 117, and morpholino 118, whose calculated log Ps ranged from 2.0 to 3.9. The SAR exhibited substantially greater flexibility than observed in the 4-aminoquinoline series (Table 4) and many of these analogs including 113-116 had respectable MICs ranging from 1-2 μg/mL (Table 8). Some of the analogs were exceptionally potent including fluoropyridine analog 112 and 4-(trifluoromethyl)cyclohex-1-yl-amino 117 whose MICs range from less than 0.06 to 0.12 μg/mL. Lastly, Applicants prepared 123 incorporating a 7-fluoro substituent in place of the trifluoromethyl group of 111 in an attempt to further modulate the lipophilicity. Gratifyingly, 123 maintains exceptional potency with an MIC of less than 0.06 μg/mL while the calculated log P decreased to 3.0. Collectively, the results from the last series of 5-aminoquinoline-4-one demonstrate high antibacterial activity can be achieved by introduction of appropriate substituents at C-5 of this scaffold and that the C-5 position is permissive to modification tolerating more polar as well as nonplanar groups.

TABLE 8

5 and 7 Substituted Quinolinones.

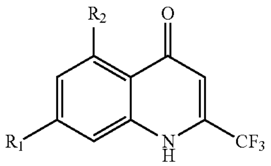

| Compound | $R_1$ | $R_2$ | MIC μg/mL | cLogP |
|---|---|---|---|---|
| 108 | $CF_3$ | 3,4-dichloroanilino | <0.06 | 5.2 |
| 109 | $CF_3$ | 3,4-difluoroanilino | <0.06 | 4.1 |
| 110 | $CF_3$ | 3-(trifluoromethoxy)anilino | <0.06-0.12 | 4.9 |
| 111 | $CF_3$ | 5-(trifluoromethyl)pyridin-2-yl-amino | <0.06 | 3.8 |
| 112 | $CF_3$ | 5-(fluoro)pyridin-2-yl-amino | 0.12 | 3.1 |
| 113 | $CF_3$ | 5-dimethylaminopyridin-2-yl-amino | 2 | 3.6 |
| 114 | $CF_3$ | 6-(trifluoromethyl)pyridazine-3-yl- | 1 | 2.9 |
| 115 | $CF_3$ | (N,N-dimethyl-6-sulfamoyl)pyridin-2- | 2 | 2.1 |
| 116 | $CF_3$ | 1H-indazol-4-yl-amino | 2 | 3.6 |
| 117 | $CF_3$ | 4-(trifluoromethyl)cyclohexyl-amino | <0.06 | 3.9 |
| 118 | $CF_3$ | morpholino | >32 | 2.0 |
| 119 | 3,4-dichloroanilino | $CF_3$ | 1 | 5.2 |
| 120 | 3,4-difluoroanilino | $CF_3$ | 4 | 4.1 |
| 121 | 3- | $CF_3$ | 1 | 4.9 |
| 122 | 5- | $CF_3$ | 4 | 3.8 |
| 123 | F | 5-(trifluoromethyl)pyridin-2-yl-amino | <0.06 | 3.1 |

Applicants selected a few of the most potent compounds from the 4-aminoquinoline (22, 31) and 5-aminoquinolin-4-one (111, 123) series for evaluation against a panel of other MRSA strains and representative gram-positive and gram-negative pathogens (Table 9). Compounds 111 and 123 show excellent activity (MIC<0.06 μg/mL) towards all six *S. aureus* strains while 31 also displays very good activity with MICs ranging from 0.125-0.25 μg/mL. The compounds maintain activity against *Staphylococcus epidermidis*; however, 31, 111 and 123 all lose considerable potency against *Enterococcus faecalis* and *Enterococcus faecium*, which contribute heavily, along with MRSA, to healthcare-associated infections. The compounds are inactive against the gram-negative bacilli *Escherichia coli, Klebsiella pneumoniae*, and *Enterococcus cloacae* as well as the fungus *Candida albicans* at the highest concentration tested.

TABLE 9

Antimicrobial Susceptibility.

| | | MIC (μg/mL) | | | |
|---|---|---|---|---|---|
| Species | Strain | 22 | 31 | 111 | 123 |
| *S. aureus* | FPR3757 | 0.06 | 0.25 | <0.06 | <0.06 |
| | MW2 | 0.125 | 0.125 | <0.06 | <0.06 |
| | COL | — | — | <0.06 | <0.06 |
| | N325 | — | — | <0.06 | <0.06 |
| | NRS71 | — | — | <0.06 | <0.06 |
| | NIH04008 | 0.125 | 0.125 | <0.06 | <0.06 |
| *S. epidermidis* | NIH04003 | — | — | <0.06 | <0.06 |
| *E. faecalis* | SMC374 | 0.125 | 2 | — | — |
| | DHMC #1 | — | — | 2 | 8 |
| *E. faecium* | ATCC19579 | 0.125 | 0.25-1 | — | — |
| | DHMC #1 | — | — | 2 | 8 |

TABLE 9-continued

| Antimicrobial Susceptibility. | | | | | |
|---|---|---|---|---|---|
| | | MIC (μg/mL) | | | |
| Species | Strain | 22 | 31 | 111 | 123 |
| *E. coli* | DHMC-1 | >4 | >64 | — | — |
| *K. pneumonia* | 7117 | >4 | >64 | — | — |
| *E. cloacae* | ND-21 | >4 | >64 | — | — |
| *C. albicans* | | >16× MIC | >16× MIC | — | — |

Figure 4:
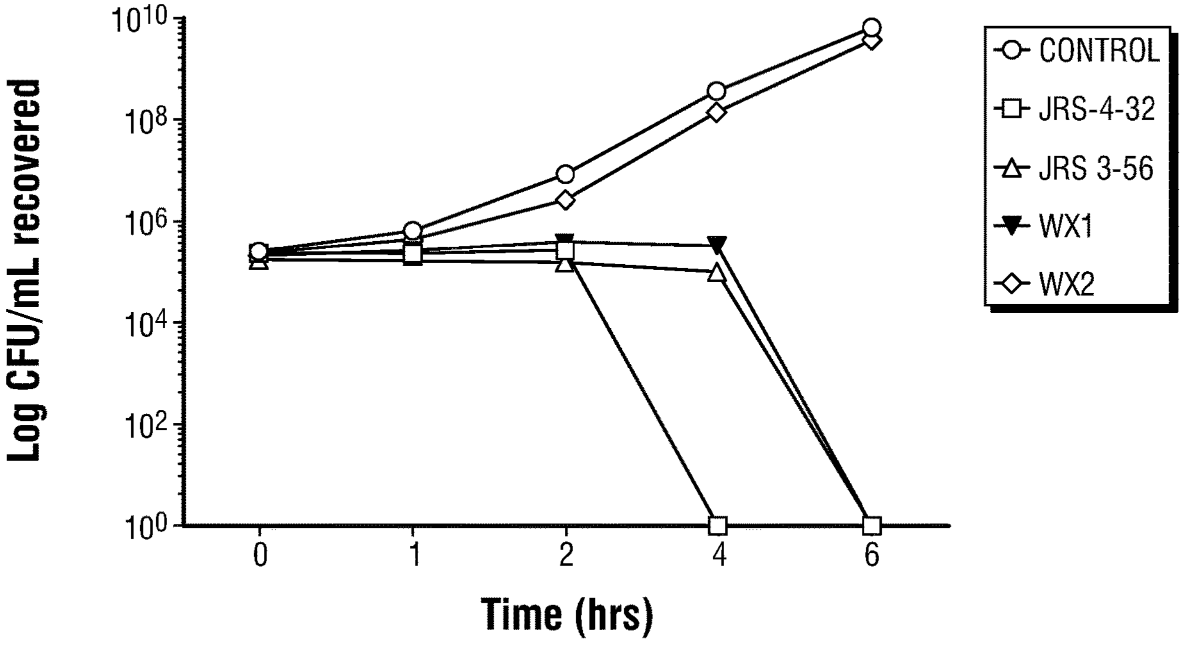
FIG. 4 illustrates in vitro time-kill analysis of methicillin resistant *Staphylococcus aureus* (MRSA). Bacterial killing was monitored by measuring the colony forming unit (CFU) for six hours when treated with compounds 22, 31, 117, and 123 at 1× the minimum inhibitory concentration (MIC) of each compound. The CFU at each time point was determined by plating and then compared to a dimethyl sulfoxide (DMSO) control.

While the MIC data confirmed that these compounds were at least bacteriostatic, Applicants wanted to test for bactericidal properties of both the aminoquinoline and aminoquinolone scaffolds. The minimum bactericidal concentration (MBC) of 22, 31, 117 and 123 was evaluated against the MRSA clinical strain *S. aureus* FPR3757. Compounds 22, 31, and 123 showed potent bactericidal activity with MBCs equal to their MIC values. The kinetics of bacterial killing was assessed in vitro using time-kill assays by incubating compounds at 1× their MIC with an initial inoculum of $10^5$ colony forming units (CFU) of *S. aureus* and removing aliquots at various time points to determine the residual CFU by plating. Compounds 22, 31, and 123 were bactericidal and reduced the CFU below the limit of detection at four to six hours (FIG. 4).

Example 1.5. Mechanism of Action Studies

Figure 5:
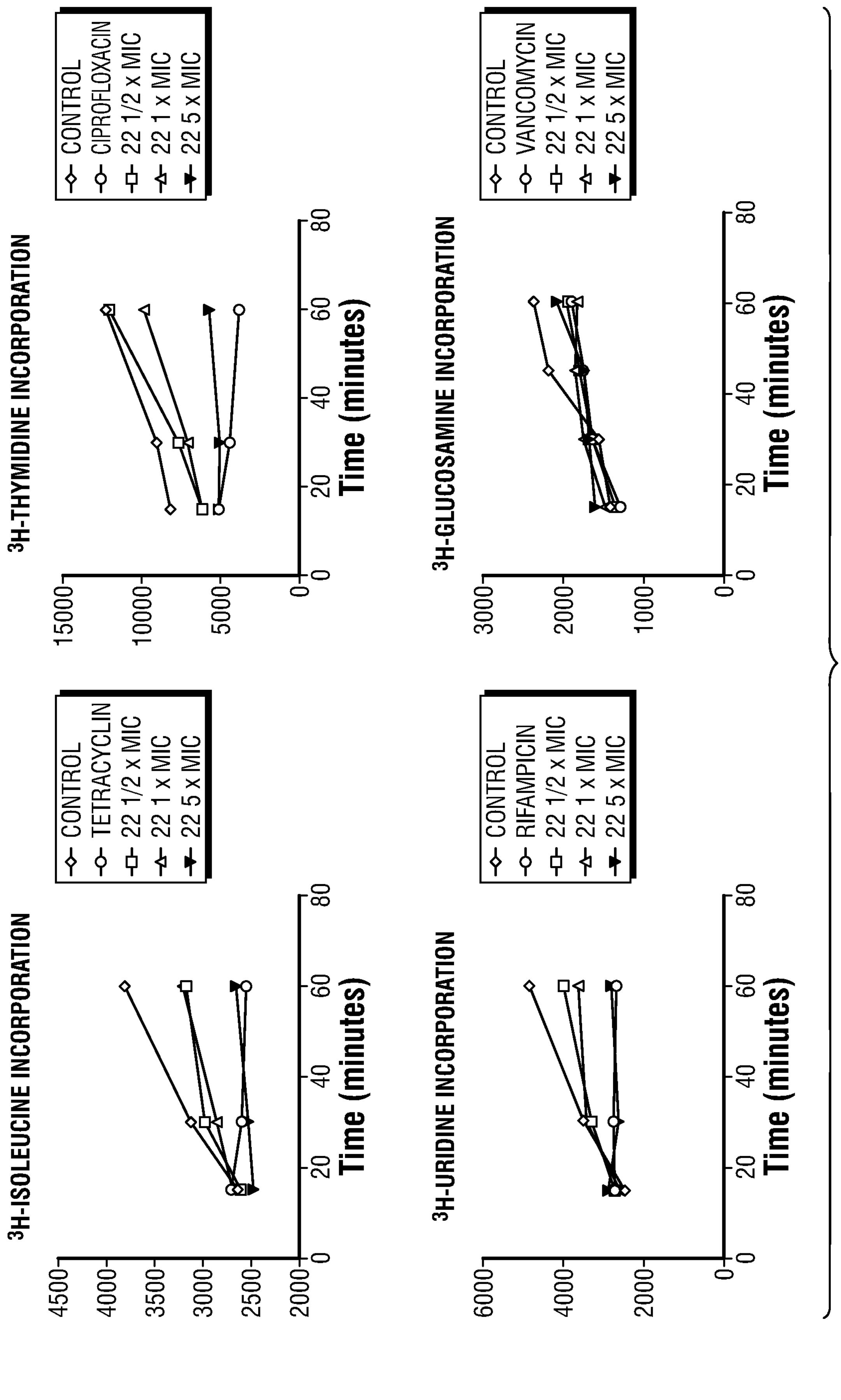
FIG. 5 illustrates macromolecular synthesis assays (representative data with 123). Time-course for inhibition of incorporation of radiolabeled precursors [$^3$H]-L-isoleucine (protein), [$^3$H]-thymidine (DNA), [$^3$H]-uridine (RNA), and [$^3$H]-glucosamine (cell wall) in *S. simulans* by 123 at 0.5×, 1× and 5×MIC. Data are expressed as the percentage of inhibition relative to the DMSO only negative control. The positive control antibiotics denoted by closed circles were used at 10× MIC. Data represent the mean±standard deviation (SD) of triplicate experiments.

Classical macromolecular synthesis assays were performed to provide insight on the putative mechanism of action of the most promising quinoline 31 and quinolone 123 candidates. Disruption of bacterial membranes is not only rapid, but interferes with all major metabolic activities in the cell and is thus easily distinguished by macromolecular synthesis assays. Radiolabeled precursors [$^3$H]-L-isoleucine, [$^3$H]-thymidine, [$^3$H]-uridine, and [$^3$H]-glucosamine were added to a culture of *Staphylococcus simulans* ($OD_{600}$=0.4) as a surrogate for *S. aureus* in Mueller-Hinton cation (MHC) adjusted medium at 37° C. along with compounds at 0.5×, 1× and 5×MIC. The control antibiotics ciprofloxacin, rifampicin, vancomycin and tetracycline were included as inhibitors of DNA, RNA, cell wall, and protein synthesis, respectively. The cells were quenched at various time points with 10% trichloroacetic acid (TCA), filtered, washed and the amount of precursor incorporation was quantified by scintillation counting. Cells treated with 31 or 123 show a clear concentration-dependent inhibition of DNA, RNA, protein and cell-wall synthesis (FIG. 5). At 5× the MIC both 31 and 123 completely inhibited all macromolecular processes, a profile that is consistent with disruption of the cellular membrane.

Figure 6A:
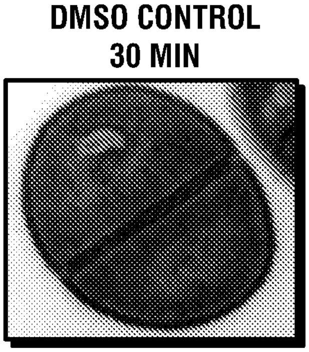
FIGS. 6A, 6B and 6C illustrate transmission electron microscopy (TEM) imaging of MRSA USA300 treated with compounds 22 and 31. Membrane disruption are highlighted with arrows by compounds 22 (FIG. 6B) and 31 (FIG. 6C) after 10 minutes (top row) and 30 minutes (bottom row) of exposure at 1×MIC compared to a DMSO control (FIG. 6A).
Figure 6B:
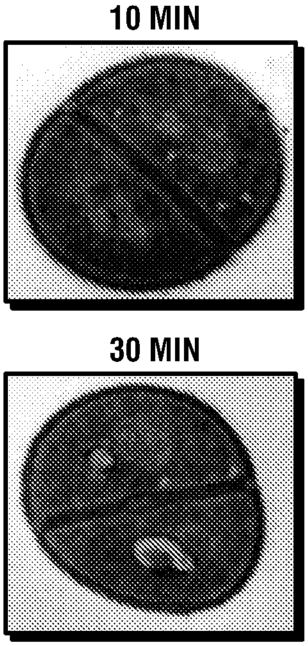
Figure 6C:
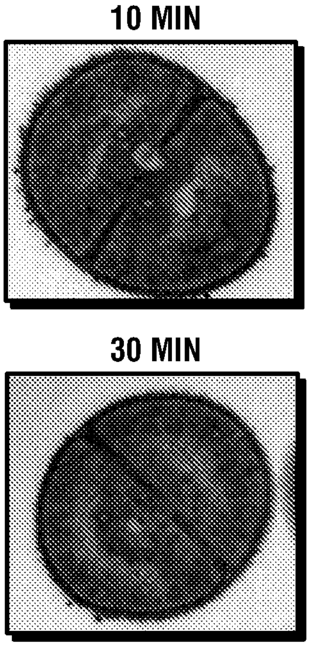

While macromolecular synthesis assays suggested membrane disruption as a likely mechanism, Applicants wanted to provide additional evidence for bacterial membrane damage. Transmission electron microscopy (TEM) and fluorescence microscopy (FM) allowed Applicants to directly observe the effects of the novel 4-aminoquinolines on 5-aminoquinolones on the cell morphology of staphylococci. *S. aureus* (strain USA300) cells treated with 31 and 123 after 10 minutes displayed cross-wall-septum formation with reduced splitting compared to the untreated cells in TEM images (FIGS. 6A, 6B, and 6C).

Figure 7A:
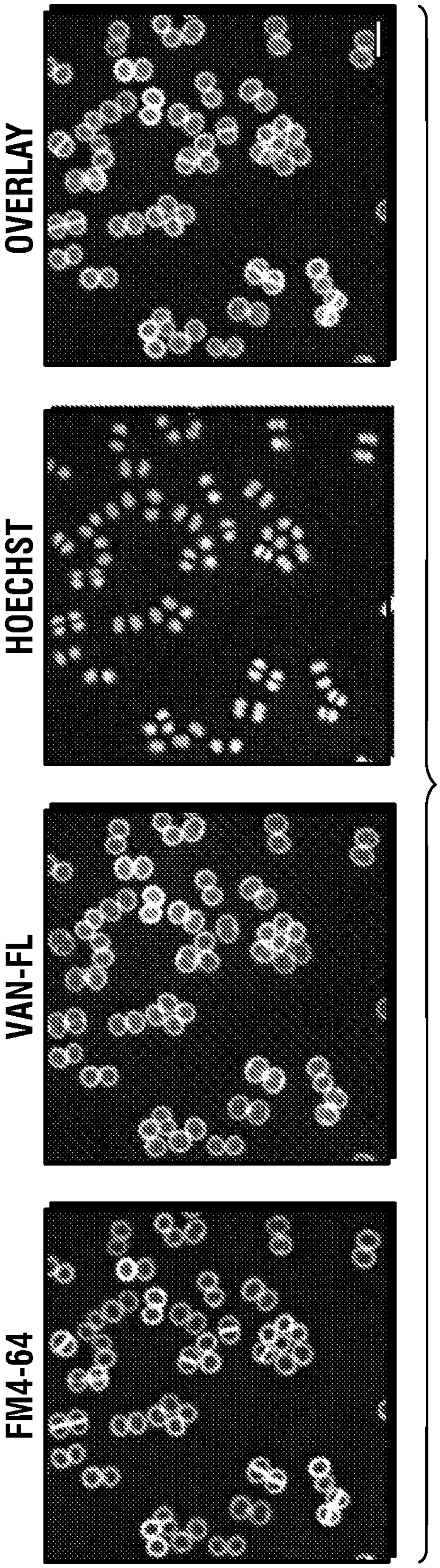
FIGS. 7A and 7B illustrate fluorescent microscopy (FM) analysis of the membrane, cell wall, and DNA in MRSA. FM of COL MRSA strain treated with compound 123 (FIG. 7B, bottom row) at 1×MIC and DMSO (FIG. 7A, top row) for 30 minutes followed by staining with FM-64 (far left column, 0.5 μg/mL), VanFL (second column, 1 μg/mL), and Hoechst (third column, 1 μg/mL) for 5 minutes and washed with 1× phosphate buffered saline (PBS) before imaging (fourth column, overlay).
Figure 7B:
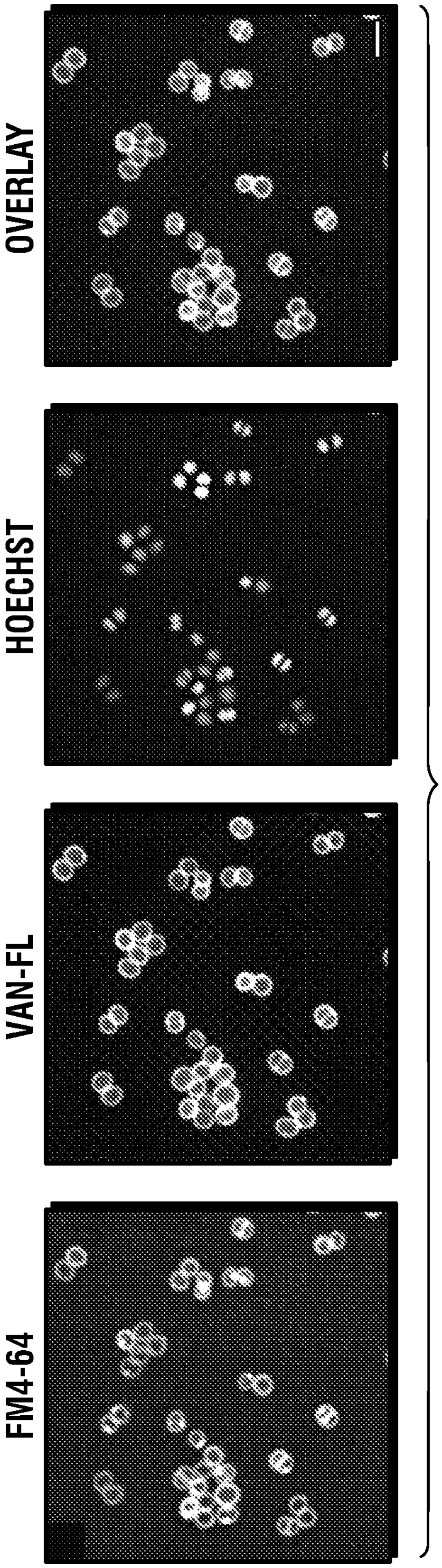

Cells treated with 31 and 123 cells also displayed mesosome-like membrane inclusions, membrane "wrinkling," and bulging of the septum (arrows). These cellular defects were not seen in any of the control cells treated with DMSO. Fluorescent microscopy was performed on a *S. aureus* (strain COL) strain after treatment with either DMSO, 31 or 123 for 30 minutes followed by staining with FM 4-64 (red membrane stain), bodipy-vancomycin (Van-FL, green stain), and Hoechst (blue DNA stain). The red membrane staining showed membrane defects (FIG. 7B) in the cells treated with 31 and 123 that included large bulges and bulging septum formation. DNA and cell wall staining showed little or no change compared to the DMSO control (FIG. 7A).

Figure 8:
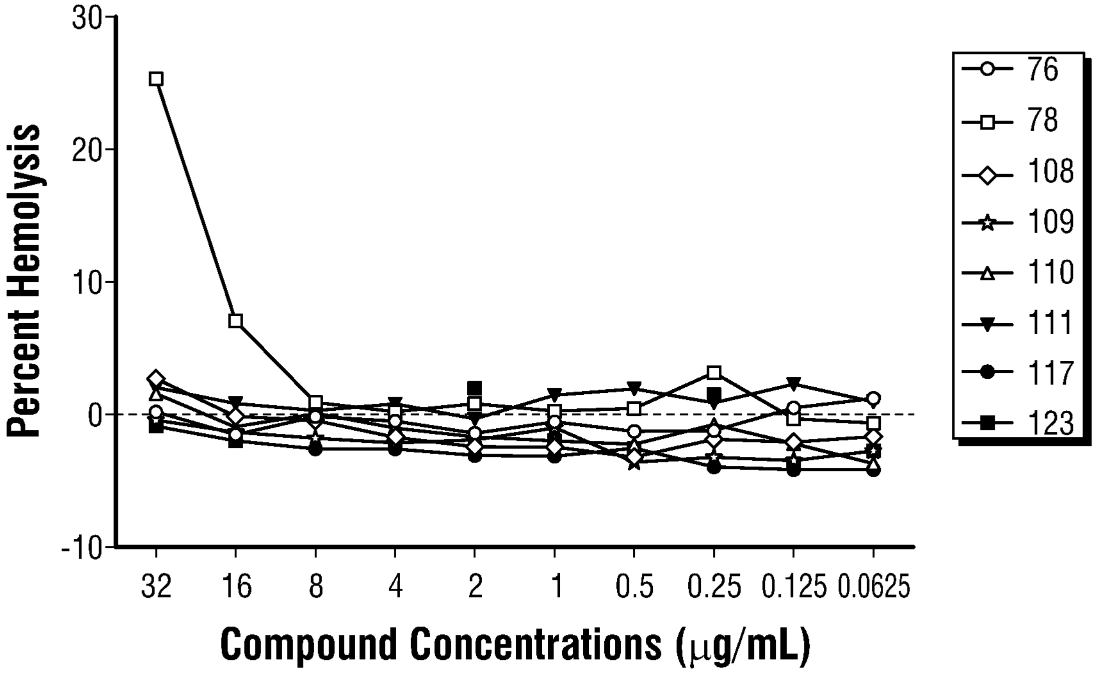
FIG. 8 illustrates percent hemolysis analysis of sheep erythrocytes. Concentration-dependent hemolysis was measured by monitoring the optical density $(OD)_{540}$ of PBS-washed sheep erythrocytes. Complete hemolysis (100%) was confirmed by treatment of erythrocytes with Triton X-100. Data points represent the mean±SD of triplicate experiments.

The macromolecular synthesis assay, TEM, and FM experiments were all consistent with membrane disruption. Applicants next sought to determine membrane selectivity of representative 4-aminoquinolines (31, 76 and 78) and the most potent 5-aminoquinolin-4-ones (108-111, 117 and 123) by a hemolytic assay employing washed sheep erythrocytes. None of the compounds except 76, displayed any hemolysis at 32 μg/mL compared to the positive control Triton X-100 (100% lysis) (FIG. 8). The promising 5-aminoquinolin-4-ones tested (108-111, 117, 123) displayed greater than 500-fold selectivity for *S. aureus* membranes over erythrocyte membranes. The high membrane selectivity of the 5-aminoquinolin-4-ones in this assay is impressive and is in accordance with the observed therapeutic index ($CC_{50}$/MIC).

Example 1.6. Conclusion

The SAR of the quinolone DNAC-2 (MIC=8 μg/mL) was systematically explored through the synthesis of more than 100 analogues that examined modification to every position of the scaffold. Strongly electron-withdrawing substituents ($CF_3$ and $OCF_3$) were optimal at the C-2 and C-7 positions while electron-donating substituents abolished activity. Introduction of a 4-arylamino group at C-4 led to a dramatic increase in potency culminating in 3,4-dichlorophenylamino 18 with an MIC of 0.06 μg/mL that was offset by a large increase in the calculated log P to 7.7. A great deal of effort was subsequently expended to maintain this outstanding activity while decreasing the lipophilicity and planarity of the molecule. Isosteric replacement of the C-4 group with a more polar 5'-(trifluoromethyl)pyridin-2-yl-amino moiety in 31 helped to decrease the calculated log P to 6.1 with an attendant 4-fold loss of potency, but non-conservative changes to introduce more polar or non-planar heterocycles were not allowed. Examination of replacements for the lipophilic 2- and 7-trifluoromethyl groups revealed 6,7-difluoro substitution of the quinoline in 78 was tolerated while reducing the calculated log P to 5.3; however, further attempts to modulate the lipophilicity through introduction of nitrogen atoms into the quinoline scaffold indicated potency and lipophilicity could not be separated. A breakthrough in the SAR was observed by synthesis of a hybrid 5-aminoquinolin-4-one scaffold by combining the quinol-4-one core of DNAC-2 with an N-aryl substituent at C-5, typified by 111 containing an 5'-(trifluoromethyl)pyridin-2-yl-amino group at C-5, whose MIC was less than 0.06 μg/mL with a calculated log P of 3.8. Further refinement led to compound 123 with equipotent activity, but a calculated log P of 3.1.

The 4-aminoquinoline and 5-aminoquinolone scaffolds represented by 31 and 123 are narrow-spectrum agents with antibacterial activity against strictly gram-positive organisms and no activity against gram-negative bacilli or fungi. Staphylococci including several multidrug-resistant MRSA strains and *S. epidermidis* are most sensitive with MICs of ≤0.06-0.12 μg/mL, but *E. faecalis*, and *E. faecium* are susceptible with MICs ranging from 2-8 μg/mL. The compounds are bactericidal with MBCs equal to the MIC values and were shown to rapidly kill staphylococci reducing the CFUs in vitro by 5-$\log_{10}$ units within the first six hours. The 4-aminoquinoline and 5-aminoquinolone are non-toxic displaying no cytotoxicity at the highest concentration evaluated providing therapeutic indexes of greater than 1000. Preliminary resistance and mechanism of action studies demonstrate these compounds selectively disrupt bacterial membrane. Overall, compound 5-aminoquinolone 123 is the most promising derivative identified from these studies based on its exceptionally potent activity, excellent therapeutic index, selective membrane-disruption and attractive physicochemical properties, which are distinguished from other membrane-active agents that tend to be large amphipathic molecules.

Example 1.7. High-Throughput Screening (HTS) Small Molecule Screening Assay

Compounds were screened as previously reported. Over 45,000 compounds from a pre-selected small molecule library at the ICCB-Longwood Screening Facility, a part of the New England Regional Centers of Excellence (NERCE), were screened for inhibition of MRSA USA300 growth. $OD_{620}$ was measured in a 384-well format. Treatment of cells with ceftoxin (32 g/ml) was used as the positive control while cells grown in Mueller-Hinton Broth (MHB) alone were used as the negative control. Per CLSI protocol, the 384-well plates were grown without shaking at 37° C. for 24 hours. Each well was scaled to respective positive and negative control to normalize the percent survival using the following equation:

$$\text{Percent survival} = \frac{(OD \text{ of the sample} - OD \text{ of positive control})}{(OD \text{ of negative control} - OD \text{ of positive control})} \times 100$$

Compounds yielding <50% survival with USA300 were considered as hits in the primary screen and further validated in the secondary screen where Applicants looked for compounds with at least 80% inhibition in growth.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of inhibiting bacterial growth in a subject, said method comprising:

administering an anti-bacterial compound to the subject, wherein the anti-bacterial compound is:

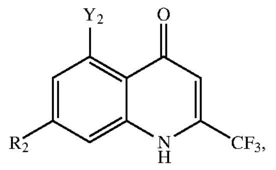

wherein $Y_2$ is selected from the group consisting of H, F, chloro, —$CHF_2$, —$CH_2F$, —$CF_3$, —$OCF_3$, —OMe, —$S(O)_2N(Me)_2$, —C(═O) OH, tetrazolyl, azido, cyano, nitro, thiomethyl, methoxy, alkyl($C_1$-$C_4$) ester, alky($C_1$-$C_4$), phenyl, cyclohexyl, pyridin-2-yl, 3,4-dichloroanilino, 3,4-difluoroanilino, 3-(trifluoromethoxy) aniline, 5-(trifluoromethyl)pyridin-2-yl-amino, 5-(fluoro)pyridin-2-yl-amino, 5-dimethylaminopyridin-2-yl-amino, 6-(trifluoromethyl)pyridazine-3-yl-amino, pyridazine-3-yl-amino, pyridazine-3-yl, (N,N-dimethyl-6-sulfamoyl)pyridin-2-yl-amino, 1H-indazol-4-yl-amino, 4-(trifluoromethyl)cyclohexyl-amino, pyrrol-2-yl, pyrrol-3-yl, pyrrol-2-ylamino, 1-methylpyrrol-2-yl, 1-methylpyrrol-3-yl, 1-methylpyrrol-2-ylamino, morpholino, piperazinyl, and —N(Me)-$R_4$;

wherein $R_2$ is selected from the group consisting of H, F, chloro, —$CHF_2$, —$CH_2F$, —$CF_3$, —$OCF_3$, —OMe, —$S(O)_2N(Me)_2$, —C(═O) OH, tetrazolyl, azido, cyano, nitro, thiomethyl, methoxy, alkyl($C_1$-$C_4$) ester, alky($C_1$-$C_4$), phenyl, 3,4-dichloroanilino, 3,4-difluoroanilino, 3-(trifluoromethoxy) aniline, 5-(trifluoromethyl)pyridin-2-yl-amino, 5-(fluoro)pyridin-2-yl-amino, 5-dimethylaminopyridin-2-yl-amino, 6-(trifluoromethyl)pyridazine-3-yl-amino, pyridazine-3-yl-amino, (N,N-dimethyl-6-sulfamoyl)pyridin-2-yl-amino, 1H-indazol-4-yl-amino, 4-(trifluoromethyl)cyclohexyl-amino, pyrrol-2-yl, pyrrol-3-yl, pyrrol-2-ylamino, 1-methylpyrrol-2-yl, 1-methylpyrrol-3-yl, 1-methylpyrrol-2-ylamino, morpholino, and piperazinyl;

wherein $R_4$ is selected from the group consisting of 5-(trifluoromethyl)pyridin-2-yl, phenyl, and cycloalkyl, and wherein the bacteria comprise Gram-positive ($Gram^+$) bacteria.

2. The method of claim 1, wherein the $Gram^+$ bacteria is selected from the group consisting of antibiotic resistant $Gram^+$ bacteria, *Enterococcus faecium, Staphylococcus epidermidis*, methicillin-resistant *Staphylococcus aureus* (MRSA), methicillin-susceptible *Staphylococcus aureus*, or combinations thereof.

3. The method of claim 1, wherein the method is used to treat or prevent a $Gram^+$ bacterial infection in the subject.

4. The method of claim 3, wherein the subject is suffering from the Gram+ bacterial infection, and wherein the method is used to treat the Gram+ bacterial infection in the subject.

5. The method of claim 1, wherein the administering is selected from the group consisting of intravenous administration, subcutaneous administration, transdermal administration, topical administration, intraarterial administration, intrathecal administration, intracranial administration, intraperitoneal administration, intraspinal administration, intranasal administration, intraocular administration, oral administration, intratumor administration, and combinations thereof.

6. The method of claim 1, wherein the anti-bacterial compound is co-administered to the subject with one or more active agents.

7. The method of claim 6, wherein the one or more active agents comprise an antibiotic.

8. The method of claim 1, wherein the anti-bacterial compound is:

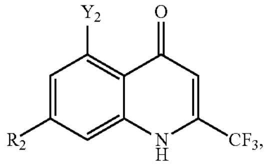

wherein $Y_2$ is —N(Me)-$R_4$, wherein $R_4$ is selected from the group consisting of 5-(trifluoromethyl)pyridin-2-yl, phenyl, and cycloalkyl, and wherein $R_2$ is $CF_3$ or chloro.

9. The method of claim 1, wherein the anti-bacterial compound is:

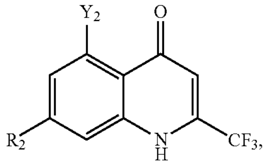

wherein $Y_2$ is —N(Me)-$R_4$, wherein $R_4$ is 5-(trifluoromethyl)pyridin-2-yl, and wherein $R_2$ is $CF_3$.

10. The method of claim 7, wherein the antibiotic is selected from the group consisting of daptomycin, vanomycin, and combinations thereof.

* * * * *